(12) United States Patent
Thompson et al.

(10) Patent No.: US 7,011,897 B2
(45) Date of Patent: Mar. 14, 2006

(54) ORGANIC LIGHT EMITTING MATERIALS AND DEVICES

(75) Inventors: Mark E. Thompson, Anaheim Hills, CA (US); Peter Djurovich, Long Beach, CA (US); Raymond Kwong, Plainsboro, NJ (US); Yeh-Jiun Tung, Princeton, NJ (US); David B. Knowles, Apollo, PA (US); Jason Brooks, Lambertville, NJ (US); Robert W. Walters, Export, PA (US); Bin Ma, Monroeville, PA (US)

(73) Assignees: The University of Southern California, Los Angeles, CA (US); Universal Display Corporation, Ewing, NJ (US)

( * ) Notice: Subject to any disclaimer, the term of this patent is extended or adjusted under 35 U.S.C. 154(b) by 0 days.

(21) Appl. No.: 10/643,413

(22) Filed: Aug. 18, 2003

(65) Prior Publication Data

US 2004/0121184 A1   Jun. 24, 2004

Related U.S. Application Data

(63) Continuation-in-part of application No. 10/288,785, filed on Nov. 6, 2002, now Pat. No. 6,916,554.

(60) Provisional application No. 60/404,213, filed on Aug. 16, 2002.

(51) Int. Cl.
C09K 11/06 (2006.01)
H05B 33/14 (2006.01)

(52) U.S. Cl. ............ 428/690; 428/917; 313/504; 546/4; 252/301.16; 257/40; 257/102

(58) Field of Classification Search .......... 428/690, 428/917; 313/504; 546/4; 252/301.16; 257/40, 102
See application file for complete search history.

(56) References Cited

U.S. PATENT DOCUMENTS

| | | | |
|---|---|---|---|
| 4,769,292 A | 9/1988 | Tang et al. | 428/690 |
| 5,247,190 A | 9/1993 | Friend et al. | 257/40 |
| 5,703,436 A | 12/1997 | Forrest et al. | 313/506 |
| 5,707,745 A | 1/1998 | Forrest et al. | 428/432 |
| 5,834,893 A | 11/1998 | Bulovic et al. | 313/506 |
| 5,844,363 A | 12/1998 | Gu et al. | 313/506 |
| 6,013,982 A | 1/2000 | Thompson et al. | 313/506 |
| 6,087,196 A | 7/2000 | Sturm et al. | 438/29 |
| 6,091,195 A | 7/2000 | Forrest et al. | 313/504 |
| 6,097,147 A | 8/2000 | Baldo et al. | 313/506 |
| 6,294,398 B1 | 9/2001 | Kim et al. | 438/22 |
| 6,303,238 B1 | 10/2001 | Thompson et al. | 428/690 |
| 6,337,102 B1 | 1/2002 | Forrest et al. | 427/64 |
| 6,468,819 B1 | 10/2002 | Kim et al. | 438/22 |
| 2002/0024293 A1 | 2/2002 | Igarashi et al. | 313/483 |
| 2002/0028329 A1 | 3/2002 | Ise et al. | 428/336 |
| 2002/0121638 A1 * | 9/2002 | Grushin et al. | 257/40 |
| 2003/0059646 A1 * | 3/2003 | Kamatani et al. | 428/690 |
| 2003/0108771 A1 * | 6/2003 | Lecloux et al. | 428/690 |
| 2003/0230980 A1 | 12/2003 | Forrest et al. | 313/600 |
| 2004/0174116 A1 | 9/2004 | Lu et al. | 313/506 |

FOREIGN PATENT DOCUMENTS

| | | |
|---|---|---|
| EP | 1 191 613 | 3/2002 |
| WO | 02/02714 | 1/2002 |
| WO | 02/15645 | 2/2002 |

OTHER PUBLICATIONS

U.S. Appl. No. 60/215,362.*
U.S. Appl. No. 60/347,910.*
M.A. Baldo et al., "Highly efficient phosphorescent emission from organic Electroluminescent devices," Nature, Sep. 1998, vol. 395, pp. 151-154.
M.A. Baldo et al., "Very high-efficiency green organic light-emitting devices based on electrophosphorescence", Applied Physics Letters, vol. 75, No., 1, pp. 4-6, Jul. 5, 1999.
C. Adachi et al., "Nearly 100% internal phosphorescence efficiency in an organic light emitting device", J. Appl. Phys. 90, pp. 5048-5051 (Nov. 2001).
H. Zollinger, "Color Chemistry" VCH Publishers, 1991.
H, J, A, Dartnall, J.K. Bowmaker, and J.D. Mollon, Proc. Roy. Soc. B. (London), 1983, 220, 115-130.
P.L. Coe et al., "The lithiation of fluorinated benzenes and its dependence on solvent and temperature", J. Chem. Soc. Perkin Trans. I, pp. 2729-2737, 1995.
A.J. Bridges et al., "A Dramatic Solvent Effect during Aromatic Halogen-Metal Exchanges. Different Products from Lithlation of Polyfluorobromobenzenes in Ether and THF", J. Org. Chem., vol. 55, pp. 773-775, Jan. 5, 1990.

(Continued)

Primary Examiner—Marie Yamnitzky
(74) Attorney, Agent, or Firm—Kenyon & Kenyon

(57) ABSTRACT

An organic light emitting device is provided. The device has an anode, a cathode, and an emissive layer disposed between the anode and the cathode, the emissive layer further comprising an emissive material having the structure:

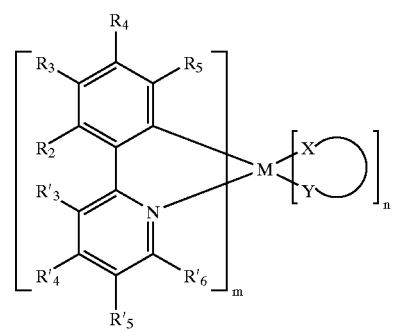

wherein each of the variables are defined herein.

73 Claims, 3 Drawing Sheets

OTHER PUBLICATIONS

Thomas H. Lowry et al., Mechanism and Theory in Organic Chemistry, Third Edition, New York, Harper & Row publishers, pp. 143-151, 1997.

N. Miyaura, et al., "Palladium-Catalyzed Cross-Coupling Reactions of Organoboron Compounds", Chem, Rev. 1995, vol. 95, No. 7, pp. 2457-2483, Nov. 1995.

D. Cuperly et al., "First Direct C-2-Lithiation of 4-DMAP. Convenient Access to Reactive Functional Derivatives and Ligands", J. Org. Chem. 2002, vol. 67, No. 1, pp. 238-241, Jan. 11, 2002.

C. Hansch, et al., "A Survey of Hammett Substituent Constants and Resonance and Field Parameters", Chem. Rev. 1991, 91, pp. 165-195.

* cited by examiner

ORGANIC LIGHT EMITTING MATERIALS AND DEVICES

RESEARCH AGREEMENTS

The claimed invention was made by, on behalf of, and/or in connection with one or more of the following parties to a joint university-corporation research agreement: Princeton University, The University of Southern California, and Universal Display Corporation. The agreement was in effect on and before the date the claimed invention was made, and the claimed invention was made as a result of activities undertaken within the scope of the agreement.

REFERENCE TO RELATED APPLICATIONS

This application is related to and claims priority from U.S. Provisional Patent Application 60/404,213 filed Aug. 16, 2002 and is a continuation-in-part of U.S. patent application Ser. No. 10/288,785 filed Nov. 6, 2002, Now U.S. Pat. No. 6,916,554, also entitled "Organic Light Emitting Materials and Devices", each of which is incorporated herein in its entirety.

FIELD OF THE INVENTION

The present invention is directed to phosphorescence based organic light emitting materials and devices that have improved electroluminescent characteristics.

BACKGROUND

Opto-electronic devices that make use of organic materials are becoming increasingly desirable for a number of reasons. Many of the materials used to make such devices are relatively inexpensive. Consequently, organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be an fluorescent or phosphorescent small molecule emitter. A dendrimer may be a "small molecule," and it is believed that all dendrimers currently used in the field of OLEDs are small molecules.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in an organic opto-electronic device. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, in a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

The technology of organic light emitting diodes (OLEDs) is undergoing rapid development. OLEDs originally utilized the electroluminescence produced from electrically excited molecules that emitted light from their singlet states as disclosed, for example, in U.S. Pat. No. 4,769,292. Such radiative emission from a singlet excited state is referred to as fluorescence. More recent work has demonstrated that higher power efficiency OLEDs can be made using molecules that emit light from their triplet state, defined as phosphorescence. Such electrophosphorescence makes it possible for phosphorescent OLEDs to have substantially higher quantum efficiencies than are possible for OLEDs that only produce fluorescence. This is based on the understanding that the excitons created in an OLED are produced, according to simple statistical arguments as well as experimental measurements, approximately 75% as triplet excitons and 25% as singlet excitons. The triplet excitons more readily transfer their energy to triplet excited states that can produce phosphorescence whereas the singlet excitons typically transfer their energy to singlet excited states that can produce fluorescence.

In contrast, only a small percentage (about 25%) of excitons in fluorescent devices are capable of producing the fluorescent luminescence that is obtained from a singlet excited state. The remaining excitons in a fluorescent device, which are produced in the lowest triplet excited state of an organic molecule, are typically not capable of being converted into the energetically unfavorable higher singlet excited states from which the fluorescence is produced. This energy, thus, becomes lost to radiationless decay processes that heat-up the device.

Since the discovery that phosphorescent materials could be used in an OLED, Baldo et al., "*Highly Efficient Phosphorescent Emission from Organic Electroluminescent Devices*" *Nature*, vol. 395, 151–154, 1998, there is now much interest in finding more efficient electrophosphorescent materials. OLEDs utilizing phosphorescent materials are disclosed, for example, in U.S. Pat. No. 6,303,238 which is incorporated by reference in its entirety.

Typically, phosphorescent emission from organic molecules is less common than fluorescent emission. However, phosphorescence can be observed from organic molecules under an appropriate set of conditions. It would be desirable if more efficient electrophosphorescent materials could be found, particularly materials that produce their emission in the technologically useful blue and green colors of the visible spectrum.

SUMMARY OF THE INVENTION

An organic light emitting device is provided. The device has an anode, a cathode, and an emissive layer disposed between the anode and the cathode, the emissive layer further comprising an emissive material having the structure:

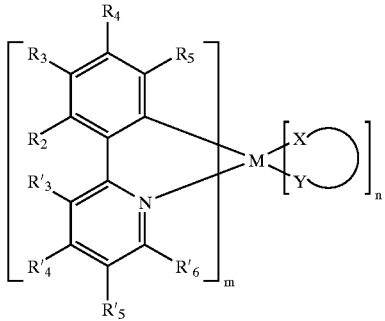

wherein M is a heavy metal with an atomic weight of greater than 40;
each of $R_2$ through $R_5$ and $R'_3$ through $R'_6$ are independently selected from the group consisting of H, halogens, CN, $CF_3$, $C_nF_{2n+1}$, trifluorovinyl, $NO_2$, $CO_2R$, $C(O)R$, $S(O)R$, $SO_2R$, $SO_3R$, $P(O)R$, $PO_2R$, $PO_3R$, C≡CR, alkyl, alkenyl, aryl, heteroaryl, aryl or heteroaryl groups substituted with halogens, CN, $CF_3$, $C_nF_{2n+1}$, trifluorovinyl, $NO_2$, $CO_2R$, $C(O)R$, $S(O)R$, $SO_2R$, $SO_3R$, $P(O)R$, $PO_2R$, or $PO_3R$, OR, SR, $NR_2$ (including cyclic-amino), $PR_2$ (including cyclic-phosphino), where R is hydrogen, an alkyl group, an aryl group or a heteroaryl group;
at least one of $R_3$ and $R_5$ is either an electron withdrawing group or an electron donating group;
m is at least 1, n is at least 0 and X-Y is an ancillary ligand.

In a preferred embodiment, $R_3$ is a substituent having a Hammett value less than about −0.17, between about −0.15 and 0.05, or greater than about 0.07.

In a further preferred embodiment, m is an integer from 1 to 4, n is an integer from 1 to 3; and,

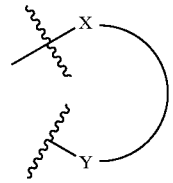

is a monoanionic ligand, preferably a non carbon coordinating ligand.

Specific embodiments of the present invention are directed to OLEDs using emissive phosphorescent organometallic compounds that produce improved electrophosphorescence in the blue region of the visible spectrum. The emissive material itself is also provided. The emissive material may have improved stability, and may provide a saturated blue emission.

Another preferred embodiment of the present invention comprises a device with an emissive material having the structure:

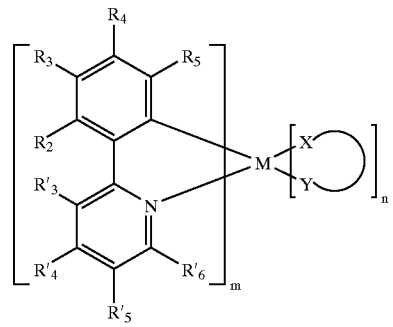

wherein M is a heavy metal with an atomic weight of greater than or equal to 40; m is at least 1; n is at least 0; X-Y is an ancillary ligand; $R_2$ and $R_4$ are both F; $R_3$ is a substituent having a Hammett value less than about −0.17, between about −0.15 and 0.05, or greater than about 0.07; and each of $R_3$, $R_5$ and $R'_3$ through $R'_6$ are independently selected from the group consisting of H, halogens, CN, $CF_3$, $C_nF_{2n+1}$, trifluorovinyl, $NO_2$, $CO_2R$, $C(O)R$, $S(O)R$, $SO_2R$, $SO_3R$, $P(O)R$, $PO_2R$, $PO_3R$, C≡CR, alkyl, alkenyl, aryl, heteroaryl, aryl or heteroaryl groups substituted with halogens, CN, $CF_3$, $C_nF_{2n+1}$, trifluorovinyl, $NO_2$, $CO_2R$, $C(O)R$, $S(O)R$, $SO_2R$, $SO_3R$, $P(O)R$, $PO_2R$, or $PO_3R$; OR, SR, $NR_2$ (including cyclic-amino), $PR_2$ (including cyclic-phosphino), where R is hydrogen, an alkyl group, an aryl group or a heteroaryl group

DETAILED DESCRIPTION

Figure 1:
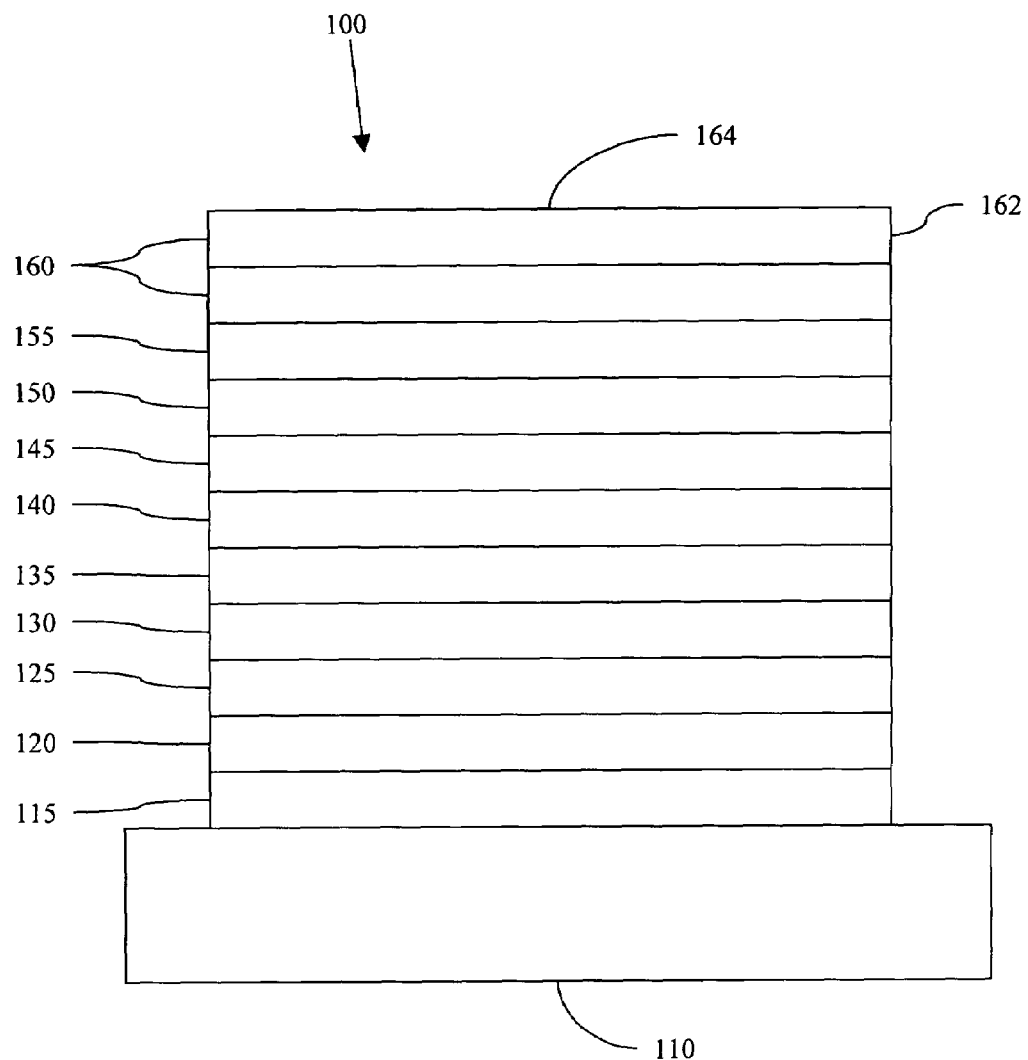
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151 154, 1998; ("Baldo I") and Baldo et al., "Very high efficiency green organic light emitting devices based on electrophosphorescence," Appl. Phys. Lett., vol. 75, No. 3, 4 6 (1999) ("Baldo II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2' bipyridine is such a molecule. Non-radiative decay mechanisms are typically temperature dependent, such that a material that exhibits phosphorescence at liquid nitrogen temperatures may not exhibit phosphorescence at room temperature. But, as demonstrated by Baldo, this problem may be addressed by selecting phosphorescent compounds that do phosphoresce at room temperature.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin orbit coupling. Such a phosphorescent transition may be observed from an excited metal to ligand charge transfer (MLCT) state of an organometallic molecule such as tris(2 phenylpyridine)iridium(III). Molecules that phosphoresce from MLCT triplet states, However, typically emit light that is of lower energy than that observed from the unbound organic ligand. This lowering of emission energy presents a challenge in the development of organic molecules that phosphoresce in the technologically useful blue and green colors of the visible spectrum where the unperturbed phosphorescence typically occurs.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. No. 5,844,363, which is incorporated by reference in its entirety. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport occurs predominantly through the highest occupied molecular orbit (HOMO) levels of the "charge carrying component" the hole transporting layer This component may be the base material of the hole transport layer 125, or it may be a dopant. Hole transport layer 125 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in U.S. patent application Ser. No. 10/173,682 to Forrest et al., which is incorporated by reference in its entirety. Other hole transport layer materials and structures may be used.

As disclosed herein, emissive layer 135 includes an organic material capable of emitting photons of light when electrons drop from a lowest unoccupied molecular orbital (LUMO) of layer 135 where they combine with holes in the highest occupied molecular orbital of layer 135. Accordingly, a current flow passed between anode 115 and cathode 160 through emissive layer 135 can produce an emission of light. In a present embodiment, emissive layer 135 comprises a phosphorescent emissive material such as those disclosed herein. Phosphorescent materials are preferred over fluorescent materials because of the higher luminescent efficiencies associated with such materials.

Emissive layer 135 may comprise a host material capable of transporting electrons and/or holes, doped with an emissive material that may trap electrons, holes, and/or excitons, such that excitons relax from the emissive material via a photoemissive mechanism. Examples of host materials include but are not limited to $Alq_3$, CBP and mCP. Alternatively, emissive layer 135 may comprise a single material that combines transport and emissive properties. Whether the emissive material is a dopant or a major constituent, emissive layer 135 may include additional materials, such as dopants that tune the emission of the emissive material Emissive layer 135 may include a plurality of emissive materials capable of, in combination, emitting a desired spectrum of light. Emissive material may be included in emissive layer 135 in a number of ways. For example, an emissive small molecule may be incorporated into a polymer. Examples of emissive and host materials known in the art are disclosed in U.S. Pat. No. 6,303,238 to Thompson et al., which is incorporated by reference in its entirety.

In a present embodiment, electron transport layer 140 may comprise a material capable of transporting electrons. Electron transport layer 140 may be intrinsic (undoped), or doped. Doping may be used to enhance conductivity. Alq3 is an example of an intrinsic electron transport layer. An example of an n-doped electron transport layer material is BPhen doped with Li at a molar ratio of 1:1, as disclosed in U.S. patent application Ser. No. 10/173,682 to Forrest et al., which is incorporated by reference in its entirety. Other electron transport layers materials and structures may be used. The charge carrying component of the electron transport layer may be selected such that electrons can be efficiently injected from the cathode into the LUMO (Lowest Unoccupied Molecular Orbital) energy level of the electron transport layer. Electron transport occurs predominantly through the lowest unoccupied molecular orbit (LUMO) levels of the "charge carrying component" of the hole transporting layer. This component may be the base material, or it may be a dopant. The LUMO level of an organic material may be generally characterized by the electron affinity of that material while the relative electron injection efficiency of a cathode may be generally characterized in terms of the work function of the cathode material. Accordingly, the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 140. Blocking layers may also be used to block excitons from diffusing out of the emissive layer.

The theory and use of blocking layers is described in more detail in U.S. Pat. No. 6,097,147 and U.S. patent application Ser. No. 10/173,682 to Forrest et al., which are incorporated by reference in their entireties. The conventional "blocking layer" is generally believed to reduce the number of charge carriers and/or excitons that leave the emissive layer by presenting an energy barrier that the charge carrier or exciton has difficulty surmounting. For example, hole transport is generally thought to be related to the Highest Occupied Molecular Orbital (HOMO) of an organic semiconductor. A "hole blocking" material may therefore be generally characterized as a material that has a HOMO energy level significantly less than that of the material from which the holes are being blocked. A first HOMO energy level is considered "less than" a second HOMO energy level if it is lower on a conventional energy level diagram, which means that the first HOMO energy level would have a value that is more negative than the second HOMO energy level. For example, through the density function theory (DFT) calculation (B3LYP 6-31G*) using the Spartan 02 software package, Ir(ppy)$_3$ has a HOMO energy level of −4.85 eV. BCP has a HOMO energy level of −5.87 eV, which is 1.02 eV less than that of Ir(ppy)$_3$, making it an excellent hole blocker. ZrQ$_4$ has a HOMO energy level of −5.00, only 0.15 eV less than that of Ir(ppy)$_3$, such that little or no hole blocking is expected. mer-GaQ$_3$ has a HOMO energy level of −4.63 eV, which is greater than that of Ir(ppy)$_3$, such that no hole blocking at all is expected.

If the emissive layer includes different materials with different energy levels, the effectiveness of these various materials as hole blocking layers may be different, because it is the difference in HOMO energy levels between the blocking layer and the blocked layer that is significant, not the absolute HOMO energy level. The absolute HOMO level, however, may be useful in determining whether a compound will be a good hole blocker for particular emissive layers. For example, a material having a HOMO energy level of about −5.15 eV or less may be considered a reasonable hole blocking material for Ir(ppy)3, which is a representative emissive material. Generally, a layer having a HOMO energy level that is at least 0.25 eV less than that of an adjacent layer may be considered as having some hole blocking properties. An energy level difference of at least 0.3 eV is preferred, and an energy level difference of at least 0.7 eV is more preferred. Similarly, the energy of an exciton is generally believed to be related to the band gap of a material. An "exciton blocking" material may generally be thought of as a material having a band gap significantly larger than the material from which excitons are being blocked. For example, a material having a band gap that is about 0.1 eV or more larger than that of an adjacent material may be considered a good exciton blocking material.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their relative ionization potential (IP) energies, with the adjacent anode layer on one side of the HIL and the hole transporting layer on the opposite side of the HIL. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., which is incorporated by reference in its entirety.

Figure 2:
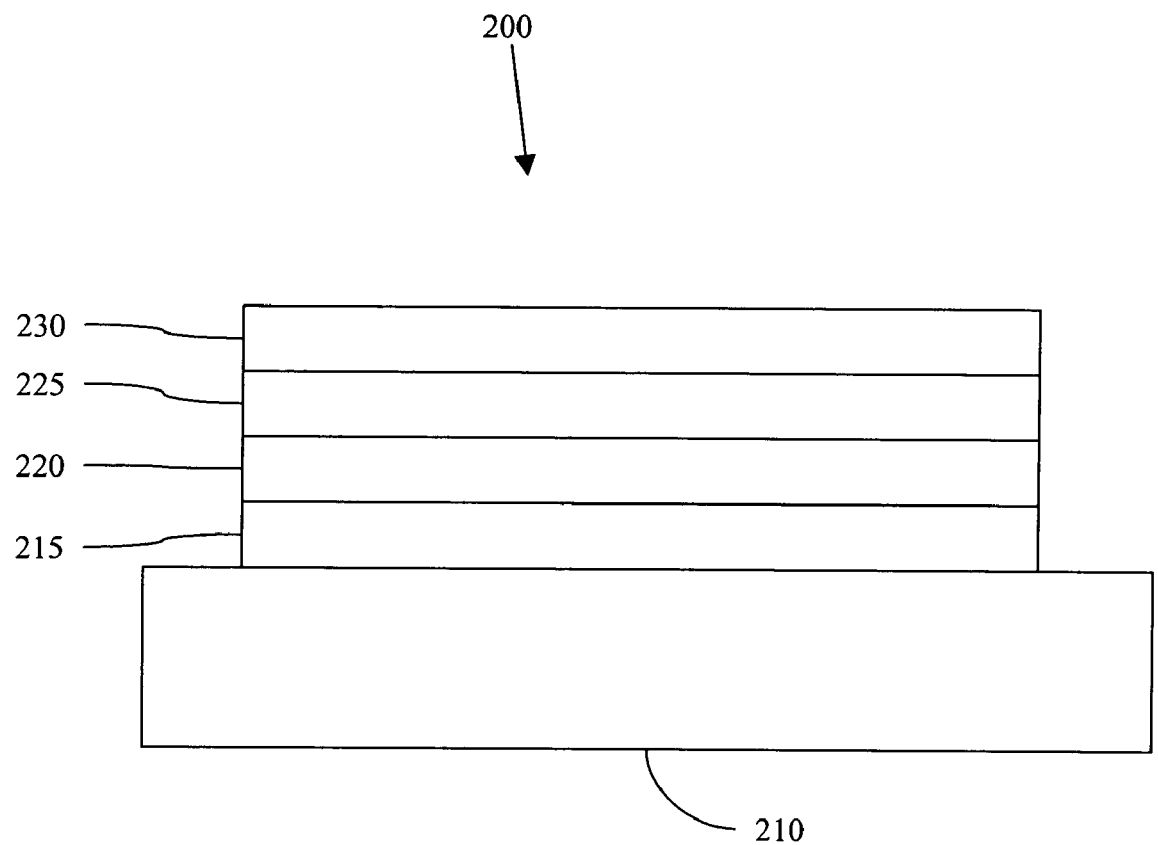
FIG. 2 shows an inverted organic light emitting device that does not have a separate electron transport layer.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation.

Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3–20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20–25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

As used herein, "solution processible" means capable of being dissolved, dispersed, or transported in and/or deposited from a liquid medium, either in solution or suspension form.

The present invention will now be described in detail for specific preferred embodiments of the invention. These embodiments are intended to be illustrative and the invention is not limited in scope to the specific preferred embodiments described.

Industry standards for full color displays call for a saturated red, green and blue emissive materials. "Saturated blue" means having a CIE coordinate of about 0.155, 0.07. However, a phosphorescent material more stable than FIrpic and having a CIE coordinate closer to saturated blue than FIrpic would be an improvement over presently available phosphorescent blue emitting materials. "Closer" to saturated blue means having CIE coordinates that are a smaller distance from 0.155, 0.07. For example, the distance between FIrpic (CIE 0.17, 0.32) and saturated blue is the square root of $((0.17-0.155)^2+(0.32-0.07)^2)$, or about 0.25044. So, a stable material having a distance less than about 0.25, and more preferably less than about 0.125, would be a desirable improvement. Another way to measure the color of emission is by peak wavelength. But, a peak wavelength measurement does not include certain useful information. For example, two different materials may emit spectra having the same peak wavelength, yet the emissions may appear different to the human eye because of the shape of the rest of the emission spectra. For example, two materials may have a peak wavelength of 470 nm. One material may have a sharp peak with very little tail into higher wavelengths, resulting in a saturated blue. The other material may have an extended tail into higher wavelengths, giving it an undesirable greenish tinge. CIE coordinates account for these differences.

"Stability" may be measured in a number of ways. One way is an $L_{100}/L_0$ test, which measures the photoluminescent emission of a thin film of material over time for at least 100 hours, and provides a parameter indicating what percentage of the original emission is still occurring at 100 hours. As used herein, $L_{100}/L_0$ means a stability test performed at about room temperature, under a vacuum of at least $1\times10^{-5}$ Torr or in an inert gas, and where the emissive material is incorporated into a film similar to one that might be used to make an organic light emitting device.

Many phosphorescent blue emitting materials generally have shortcomings, such as insufficient stability, or insufficient color saturation. One blue emitting phosphorescent material is FIrpic, which has the structure of Formula 1:

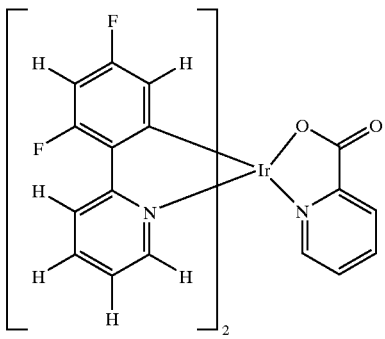

FIrpic in a non-polar solvent emits a photoluminescent spectrum at CIE 0.17, 0.32. FIrpic doped at 6% into CBP has an $L_{100}/L_0$ stability of 71% at an initial photoluminescent (PL) intensity of about 20 cd/m2.

In one embodiment of the present invention, a method is provided for modifying FIrpic and similar materials based on metals other than Ir. The modification may increase stability and/or tune the color emitted by the material. The substituted molecule has the following structure of Formula 2:

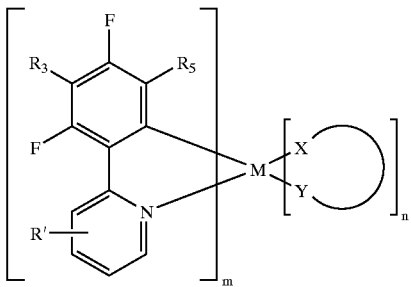

M may be any metal having an atomic weight greater than 40. Preferred metals include Ir, Pt, Pd, Rh, Re, Ru, Os, Tl, Pb, Bi, In, Sn, Sb, Te, Au, and Ag. More preferably, the metal is Ir or Pt. Most preferably, the metal is Ir.

$R_3$ may be any substituent, i.e., $R_3$ is not H. Preferably, any substituent other than $CH_3$ and F may be used. More preferably, the substituent may be selected from the group consisting of alkyl, alkoxy, amino, carboxy, cyano, aryls, and 5 and 6 member heteroaryls. Aryls include phenyl and napthyl. Heteroaryls include pyridine, pyrimidine and pyridazine. Any of these substituents may be further substituted. The relatively low stability of FIrpic is believed to be due in part to the two fluorine atoms on the phenyl ring. It has be documented that fluorine exerts the strongest acidifying effect between all of the halogens on an aromatic ring and specifically influences the acidifying effect at the ortho positions. When the fluorine groups are in a 1,3 relationship, hydrogen abstraction occurs in between at the two position. See Coe, P. L. et al, *J. Chem. Soc. Perkin Trans.* 1, 1995 pp. 2729–2737 and Bridges, A. J.; *J. Org. Chem,* 1990, 55 773–775. In the molecule FIrpic the same acidifying effect is observed, that is the hydrogen atom in the 3 position (between the two fluorines illustrated below as $R_3$) can be readily removed leading to instability. By substituting this hydrogen atom with a group that is less easily removed, the stability problem may be mitigated.

In a preferred embodiment, $R_3$ may be a group in which the atom connected to the phenyl ring possesses a non-empty p-orbital or n-orbital that may be in π-conjugation or partial π-conjugation with the π-system in the phenyl ring. It is believed that such an $R_3$ substituent leads to enhanced stability. One example of such a substituent has a carbon in the $R_3$ substituent bound to the carbon in the 3 position, where the carbon in the $R_3$ substituent is bound to at least one other atom with at least a double bond, or is part of a resonating structure such as a phenyl ring. The double bond or resonating structure alters the orbital structure such that there is π-conjugation or partial π-conjugation with the π-system in the phenyl ring and the carbon in the substituent to which it is bound. Cyano and phenyl substituents provide examples of such a bonding arrangement. Another example of such a substituent is one having a lone pair of electrons, such as an oxygen atom or a nitrogen atom.

$R_5$ may be H or any substituent. Where a blue-emitting material is desired, preferred substituents for the $R_5$ position electron withdrawing groups. The substituents may be further substituted.

R' may be H or any substituent. R' may represent substitution at any number of sites on the pyridyl ring, including mono-, di-, tri-, and tetra-substitution. Where there is more than one substituent, multiple substituents may be linked to each other. Where a blue emitting material is desired, preferred substituents include electron donating groups. Examples of electron donating groups (when attached to the carbon para to the nitrogen) include methyl, methoxy, amino, dialkylamino, and 5 or 6 member cyclic amino groups such as morpholino, pyrrolidino, piperidino. Whether a group is electron donating or electron withdrawing may depend upon the position to which it is attached.

The (X-Y) ring in Formula 2 may be referred to as an "ancillary ligand." (X-Y) may be any mono-anionic ligand. The ligand is referred to as "ancillary" because it is believed that it may modify the photoactive properties of the material, as opposed to directly contributing to the photoactive properties. By way of contrast, the ligand to the left is referred to as "photoactive" because it is believed that it contributes to the photoactive properties of the material. Although Formula 2 illustrates a bidentate ancillary ligand, other structures may be used. The definitions of photoactive and ancillary are intended as non-limiting theories.

The subscripts "m" is the number of photoactive ligands of a particular type, and "n" is the number of ancillary ligands of a particular type. Depending upon the metal M, a certain number of ligands may be attached to the metal. Generally, the ligands are bidentate, which means that they form two bonds with the metal, but bidentate ligands are not required. For example, two chlorines could be attached to the metal in place of a bidentate ancillary ligand. "m" is at least one, and may be any integer greater than zero up to the maximum number of ligands that may be attached to the metal. "n" may be zero, and may be an integer greater than zero, subject to the requirement that "m" is at least one. "m"+"n" may be less than the total number of ligands that may be attached to M, such that ligands other than those specifically illustrated in Formula 2 may also be attached to M. These additional ligands may be photoactive or ancillary.

For iridium, to which 3 bidentate ligands may be attached, "m" may be 1, 2 or 3, and "n" may be 0, 1 or 2.

The photoactive ligand in Formula 2 has the structure of Formula 3:

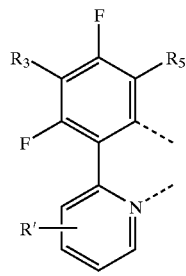

Preferred ancillary ligands include acetylacetonate (acac), picolinate (pic) and dipivaloylmetanate (t-butyl acac). Some preferred ancillary ligands have the following structure according to Formula 4 (pic), Formula 5 (acac), and Formula 6 (t-butyl acac). Other ancillary ligands may be used. Further non-limiting examples of ancillary ligands may be found in PCT Application Publication WO 02/15645 A1 to Lamansky et al. at pages 89–90, which are incorporated herein by reference:

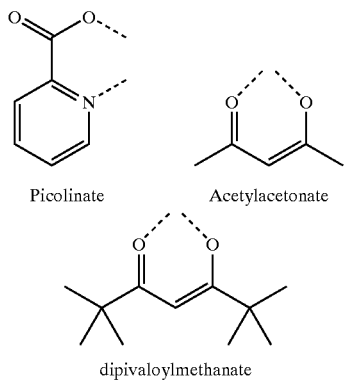

Picolinate    Acetylacetonate dipivaloylmethanate

In a preferred embodiment of Formula 2, n is zero, and m is the maximum number of ligands that may be attached to the metal. For example, for Ir, m is three in this preferred embodiment, and the structure may be referred to as a "tris" structure. The tris structure is preferred because it is believed to be particularly stable. The stability of the tris structure, combined with the stability and color tuning provided by the $R_3$ group, may result in a particularly stable blue emitting phosphorescent material.

In one embodiment of formula 2, m+n is equal to the total number of bidentate ligands that may be attached to the metal in question—for example, 3 for Ir. In another embodiment, m+n may be less than the maximum number of bidentate ligands that may be attached to the metal, in which case other ligands—ancillary, photoactive, or otherwise—may also be attached to the metal. Preferably, if there are different photoactive ligands attached to the metal, each photoactive ligand has the structure indicated in Formula 3.

In addition to enhancing stability, the $R_3$ substituent group may be used to tune the color of light emitted by the material. It is believed that an $R_3$ substituent having a negative Hammett value may red-shift the color emission, while an $R_3$ substituent having a positive Hammett value may blue-shift the color of emission. The Hammett value of a group is a measure of whether is withdraws electrons (positive Hammett value), or donates electrons (negative Hammett value). The Hammett equation is described in more detail in: Thomas H. Lowry and Kathleen Schueller Richardson "Mechanism and Theory In Organic Chemistry," New York, 1987, pages 143–151, which is incorporated by reference. Where red-shifting is desired, a Hammett value less than −0.18 is preferred. Where blue-shifting is desired, the Hammett value is preferably greater than about 0.07, more preferably greater than about 0.2, and most preferably greater than about 0.6. These larger Hammett values are particularly desirable when a blue-emitting phosphorescent material is sought. A Hammett value having a smaller absolute value may not have a significant shifting effect. Where enhanced stability without color shifting is desired—for example, if a material already emits a desired spectra, such as saturated green—a Hammett value between about −0.16 and 0.5 is preferred. There are circumstances within the scope of the present invention where Hammett values outside of the ranges described may be appropriate.

Substituents in the $R_5$ and R' positions may also be used to tune the color emitted by the material. It is believed that the color-shifting effect of a substituent having a particular Hammett value may vary depending upon where the substituent is attached. For example, it is believed that a substituent attached to any position on the same phenyl ring as $R_3$ in FIrpic may cause a shift in the same direction—positive Hammett values correspond to blue shifting, and negative Hammett values to red shifting. But, a substituent attached to any position on the pyridyl ring may cause a shift in the opposite direction—positive Hammett values correspond to red shifting, and negative Hammett values correspond to blue shifting. Notably, the sign (and magnitude) of the Hammett value of a particular substituent may change depending upon where it is attached. The Hammett values associated with a "para" position, $\sigma_{para}$, are used for $R_3$, because $R_3$ is in the para position to the carbon coordinated to the metal.

Preferred substituents for the $R_3$ position include Ph, cyano, 4-CF$_3$Ph, and pyridine. It is believed that each of these substituents enhance stability. Each of these substituents except Ph also provides a blue shift relative to FIrpic. Ph provides a very mild red-shift, and may be useful for situations where enhanced stability without a significant color shift is desired.

A particularly preferred substituent for the $R_3$ position is a cyano group. It is believed that the cyano group advantageously provides enhanced stability, as well as a significant blue shift of about 15 nm from the unsubstituted analog. A substituted material having a photoactive ligand similar to FIrpic, with a cyano group in the 3 position, has the following structure of Formula 7. $R_5$ and R' may be H or a substituent, selected based on considerations similar to those discussed with respect to Formula 2.

Formula 7:

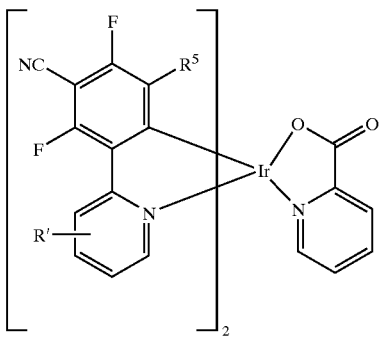

Various embodiments of the present invention may be applied to a class of materials more general than FIrpic derivatives. For example, in one embodiment of the present invention, substitutions may be made to the following material to enhance stability and/or tune color emission, in accordance with Formula 8:

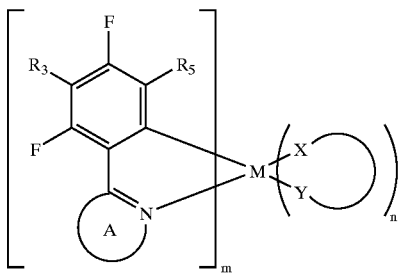

$R_3$ may be selected from the same substituents described with respect to Formula 2, for similar reasons. Phenyl and cyano groups are preferred $R_3$ substituents. $CH_3$ and F may also be used as a substituent in the $R_3$ position for materials where the bottom ring is not a 6-member pyridyl ring. The bottom ring "A" may be a heteroaryl ring system with at least one nitrogen atom that is coordinated to the metal M. Preferably, A is a 5 or 6 member heteroaryl ring system. A single or multiple additional heteroatoms, such as nitrogen or other heteroatoms, may also be incorporated. The heteroaryl ring may be benzanullated to yield various heteroaryl ring systems, such as quinoline, isoquinoline, and others. The ring may be substituted or unsubstituted in one or multiple positions. For example, such substituents may include alkyl, halogen, alkoxy, aryl, and/or heteroaryl. $R_5$ may be selected from the same substituents described with respect to Formula 2, for similar reasons.

In one embodiment of the invention, a stable phosphorescent material that emits a saturated blue is sought. In other embodiments, other colors are sought. For example, a saturated green or a saturated red may be obtained. While green and red phosphorescent materials are generally more available in the prior art than blue, embodiments of the present invention may lead to phosphorescent materials having better color saturation, better stability, or both.

Formula 2 is a preferred embodiment of the structure of Formula 8.

As noted above, various embodiments of the present invention may be applied to a class of materials more general than FIrpic derivatives. For example, an organometallic compound of the present invention can be represented by the following general Formula 9,

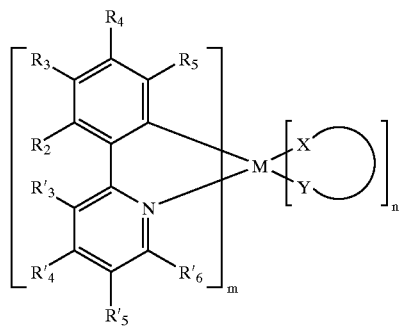

wherein M is a heavy metal with an atomic weight of greater than 40;

each of $R_2$ through $R_5$ and $R'_3$ through $R'_6$ are independently selected from the group consisting of H, halogens, CN, $CF_3$, $C_nF_{2n+1}$, trifluorovinyl, $NO_2$, $CO_2R$, $C(O)R$, $S(O)R$, $SO_2R$, $SO_3R$, $P(O)R$, $PO_2R$, $PO_3R$, C≡CR, alkyl, alkenyl, aryl, heteroaryl, aryl or heteroaryl groups substituted with halogens, CN, $CF_3$, $C_nF_{2n+1}$, trifluorovinyl, $NO_2$, $CO_2R$, $C(O)R$, $S(O)R$, $SO_2R$, $SO_3R$, $P(O)R$, $PO_2R$, or $PO_3R$, OR, SR, $NR_2$ (including cyclic-amino), $PR_2$ (including cyclic-phosphino), where R is hydrogen, an alkyl group, an aryl group or a heteroaryl group;

at least one of $R_3$ and $R_5$ is either an electron withdrawing group or an electron donating group;

m is at least 1, n is at least 0; and,

X-Y may be an ancillary ligand.

The organometallic compounds of formula 9 comprise a heavy transition metal which produces phosphorescent emission from a mixture of MLCT and π—π* ligand states. Suitable transition metals include but are not limited to Ir, Pt, Pd, Rh, Re, Os, Tl, Pb, Bi, In, Sn, Sb, Te, Au, and Ag and other heavy metals with an atomic number of at least 40. Preferably an atomic number of at least 72.

In a preferred embodiment of formula 9, m is an integer from 1 to 4, n is an integer from 1 to 3; and

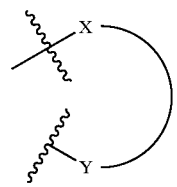

is a monoanionic non carbon coordinating ligand. In this embodiment, the metal is bound to at least one mono-anionic, bidentate, carbon-coordination ligand substituted with electron donating and/or electron withdrawing substituents that shift the emission, relative to the un-substituted ligand, to either the blue, green or red region of the visible spectrum. Further, in this embodiment, the at least one mono-anionic, bidentate, carbon-coordination ligand is substituted with at least one electron withdrawing or electron donating substituent at the $R_3$ or $R_5$ position and the metal is bound to at least one other monoanionic, preferably, non-carbon coordinating ancillary ligand that is different than the first mono-anionic, bidentate, carbon coordination ligand. Preferred ancillary ligands are include those described for formula 2.

In a further preferred embodiment of Formula 9, at least one of $R_3$ and $R_5$ is an electron withdrawing group. The other of $R_3$ and $R_5$ is the same electron withdrawing group, a different electron withdrawing group, an electron donating group or hydrogen. In a more preferred embodiment $R_3$ is an electron withdrawing group and $R_5$ is the same electron withdrawing group, a different electron withdrawing group, or hydrogen.

In one preferred embodiment of the present invention according to Formula 9, at least one of $R_2$ and $R_4$ is an electron withdrawing group. In a more preferred embodiment of the present invention at least one of $R_2$ and $R_4$ is an electron withdrawing group that is not F. In another preferred embodiment $R_4$ is an electron withdrawing group other than F.

In a further preferred embodiment $R_4$ is hydrogen.

In a preferred embodiment of the present invention according to Formula 9, the electron withdrawing group can be selected from the group consisting of halogens, CN, $CF_3$, $C_nF_{2n+1}$, trifluorovinyl, $NO_2$, $CO_2R$, $C(O)R$, $S(O)R$, $SO_2R$, $SO_3R$, $P(O)R$, $PO_2R$, or $C\equiv CR$, aryl or heteroaryl groups substituted with halogens, CN, $CF_3$, $C_nF_{2n+1}$, trifluorovinyl, $NO_2$, $CO_2R$, $C(O)R$, $S(O)R$, $SO_2R$, $SO_3R$, $P(O)R$, $PO_2R$, or $PO_3R$, where R is hydrogen, an alkyl group, an aryl group or a heteroaryl group but is not limited to the group listed.

In a further preferred embodiment of the present invention according to Formula 9, at least one of $R_3$ and $R_5$ is an electron withdrawing group or an electron donating group and $R'_4$ is an electron withdrawing group or an electron donating group. In a more preferred embodiment, at least one of $R_3$ and $R_5$ is an electron withdrawing group or an electron donating group and $R'_4$ is an electron withdrawing group or an electron donating group such that if neither $R_3$ nor $R_5$ is an electron donating group then $R'_4$ is an electron donating group and vice versa, if neither $R_3$ nor $R_5$ is an electron withdrawing group then $R'_4$ is an electron withdrawing group.

Thus, particular preferred embodiments comprise the general formula 9 where $R'_4$ is an electron withdrawing group or an electron donating group such that if neither $R_3$ nor $R_5$ is an electron withdrawing group then $R'_4$ is an electron withdrawing group and if neither $R_3$ nor $R_5$ is an electron donating group then $R'_4$ is an electron donating group.

As noted above, the Hammett value of a group is a measure of whether is withdraws electrons (positive Hammett value), or donates electrons (negative Hammett value). As with $R_3$, the Hammett values associated with a "para" position, $\sigma_{para}$, are used for $R'_4$, because $R'_4$ (like $R_3$) is in the para position to the carbon coordinated to the metal. In preferred embodiments, $R'_4$ is a strong electron withdrawing group or a strong electron donating group.

In a further preferred embodiment of the present invention according to Formula 9, the electron donating group or groups are selected from alkyl, alkenyl, aryl, heteroaryl, OR, SR, $NR_2$ (including cyclic-amino), $PR_2$ (including cyclic-phosphino), where R is hydrogen, an alkyl group, an aryl group or a heteroaryl group.

When electron withdrawing groups are placed in the $R_3$ position in formulas 2 and 9, a hypsochromic (blue) shift in the emission spectrum is observed. The unsubstituted comparative example A (See Table 1 below) has an emission wavelength of 520 nm. When an electron-withdrawing group such as a trifluoromethyl group is placed in the $R_3$ position in Formula 9, a shift towards higher energy is observed. In combination with another electron withdrawing group at the $R_5$ position an additional 40 nm hypsochromic shift occurs. The combined additive effect gives a blue/green emission of 470 nm., a blue shift of 50 nm. Other electron withdrawing groups can be incorporated into these positions to shift the emission wavelength towards higher energies. When a cyano group is incorporated into the R3 position a hypsochromic shift of 20 nm is observed, giving an emission wavelength of 500 nm. One can tune the emission by incorporating various substituted electron-withdrawing groups at either the R3 or R5 positions. In addition, one could further shift the emission wavelength by incorporating electron donating groups, especially on the pyridine ring. When a strong electron donating group such as a dimethylamino group is placed at the R'4 position a further shift towards a more saturated blue is observed giving an emission wavelength of 463 nm.

Conversely, when electron-donating groups are placed at the $R_3$ position a bathochromic (red) shift is observed. The stronger the electron donating group the greater the bathochromic shift in the emission is observed. Similarly, and in combination with substitutents on the phenyl ring, electron withdrawing groups when placed on the pyridine ring, emission spectra between 500 nm and 650 nm can be realized with the appropriate choice and location of substituents.

The compounds of the present invention are, in a preferred embodiment, intended for use in a luminescent device. Generally such a device will comprise an organic layer which comprises the compound of the present invention disposed in some manner between two electrodes, one a cathode and the other an anode. The scope of the invention is not to be limited to the theory behind the invention.

The present invention comprises, in a preferred embodiment, a light emitting device including an emissive layer comprising a organometallic compound represented by the following general structure,

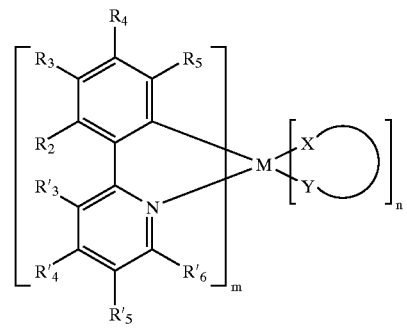

wherein M is a metal and at least one of $R_3$ and $R_5$ is either an electron withdrawing group or an electron donating group and wherein m is an integer between 1 and 4 and n is an integer between 1 and 3,; $R_4$ not being F. More specifically, $R_4$ is an electron withdrawing group selected from H, halogens, CN, $CF_3$, $C_nF_{2n+1}$, trifluorovinyl, $NO_2$, $CO_2R$, $C(O)R$, $S(O)R$, $SO_2R$, $SO_3R$, $P(O)R$, $PO_2R$, $PO_3R$, $C\equiv CR$, alkyl, alkenyl, aryl, heteroaryl, aryl or heteroaryl groups substituted with halogens, CN, $CF_3$, $C_nF_{2n+1}$, trifluorovinyl, $NO_2$, $CO_2R$, $C(O)R$, $S(O)R$, $SO_2R$, $SO_3R$, $P(O)R$, $PO_2R$, or PO$_3$R or an electron donating group selected from OR, SR, NR$_2$ (including cyclic-amino), PR$_2$ (including cyclic-phosphino), where R is hydrogen, an alkyl group, an aryl group or a heteroaryl group. In preferred embodiments,

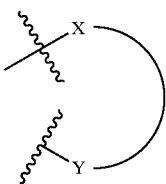

is a monoanionic non carbon coordinating ligand

In a further preferred embodiment the present invention comprises a light emitting device including an emissive layer comprising a organometallic compound represented by the following general structure,

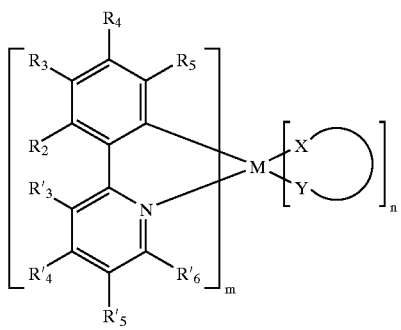

wherein M is a metal and at least one of R$_3$ and R$_5$ is either an electron withdrawing group or an electron donating group, wherein m is an integer from 1 to 4 and n is an integer from 1 to 3, and wherein R'$_4$ is an electron withdrawing or an electron donating group such that when neither R$_3$ or R$_5$ is an electron withdrawing group then R'$_4$ is an electron withdrawing group and when neither R$_3$ or R$_5$ is an electron donating group then R!$_4$ is an electron donating group. In a further preferred embodiment,

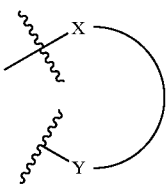

is a monoanionic non carbon coordinating ligand

The present invention comprises, in a preferred embodiment, a light emitting device including an emissive layer comprising a organometallic compound represented by the following general structure,

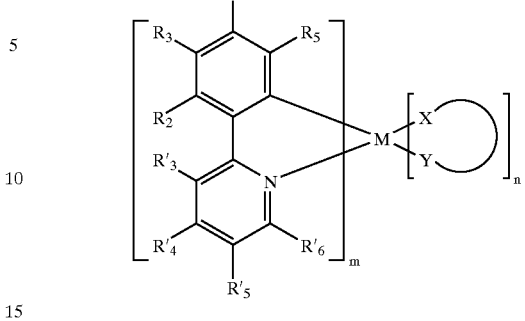

wherein M is a metal and at least one of R$_3$ and R$_5$ is selected from the group consisting of H, halogens, CN, CF$_3$, C$_n$F$_{2n+1}$, trifluorovinyl, NO$_2$, CO$_2$R, C(O)R, S(O)R, SO$_2$R, SO$_3$R, P(O)R, PO$_2$R, PO$_3$R, C≡CR, alkyl, alkenyl, aryl, heteroaryl, aryl or heteroaryl groups substituted with halogens, CN, CF$_3$, C$_n$F$_{2n+1}$, trifluorovinyl, NO$_2$, CO$_2$R, C(O)R, S(O)R, SO$_2$R, SO$_3$R, P(O)R, PO$_2$R, or PO$_3$R and wherein m is an integer between 1 and 4 and n is an integer between 1 and 3. In a further preferred embodiment,

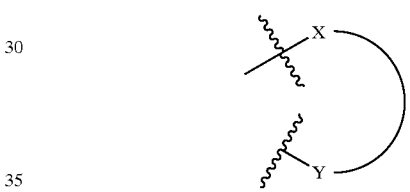

is a monoanionic non carbon coordinating ligand.

In a preferred embodiment the emissive layer comprises host material. The host material may comprise an electron transporting material that conducts charge primarily by the transport of electrons. Alternatively the host material may comprise a hole transporting material that conducts charge primarily by the transport of holes. The organometallic compound described can be doped in the host material of the light emitting device. The organometallic compound has a lowest triplet excited state with a radiative decay of greater than approximately 1×10$^5$ per second and the energy level of the lowest triplet excited state of the host material is higher than the energy level of the lowest triplet state of the organometallic compound. In a preferred embodiment of the present invention the energy difference between the lowest triplet excited state of the organometallic compound of the present invention and a corresponding relaxed state of the organometallic compound corresponds with a wavelength of less than approximately 520 nm. More preferably the energy difference between the lowest triplet excited state of the organometallic compound of the present invention and a corresponding relaxed state of the organometallic compound corresponds with a wavelength of between approximately 420 nm and approximately 480 nm.

The organic light emitting devices of the present invention may be fabricated using methods and materials known in the art. Representative OLED methods, materials and configurations are described in U.S. Pat. Nos. 5,703,436;

5,707,745; 5,834,893; 5,844,363; 6,097,147; and 6,303,238; each of which is incorporated by reference in its entirety.

The compounds described have been represented throughout by their monomeric structure. As is well known to those in the art, the compounds may also be present as dimers, trimers or dendrimers.

Aryl alone or in combination includes carbocyclic aromatic systems or heterocyclic aromatic systems (also known as heteroaryl). The systems may contain one, two or three rings wherein each ring may be attached together in a pendent manner or may be fused. Preferably the rings have 5 or 6 members.

Alkoxy includes linear or branched alkoxy groups, preferably $C_1$ to $C_6$ alkoxy groups, more preferably $C_1$ to $C_3$ alkoxy groups.

Alkyl alone or in combination includes linear or branched alkyl groups, preferably $C_1$ to $C_6$ alkyl groups, more preferably $C_1$ to $C_3$ alkyl groups.

Substituted refers to any level of substitution although mono-, di- and tri-substitutions are preferred.

Material Definitions:

As used herein, abbreviations refer to materials as follows:

| | |
|---|---|
| CBP: | 4,4'-N,N-dicarbazole-biphenyl |
| m-MTDATA | 4,4',4"-tris(3-methylphenylphenlyamino)triphenylamine |
| Alq$_3$: | 8-tris-hydroxyquinoline aluminum |
| Bphen: | 4,7-diphenyl-1,10-phenanthroline |
| n-BPhen: | n-doped BPhen (doped with lithium) |
| F$_4$-TCNQ: | tetrafluoro-tetracyano-quinodimethane |
| p-MTDATA: | p-doped m-MTDATA (doped with F$_4$-TCNQ) |
| Ir(ppy)$_3$: | tris(2-phenylpyridine)-iridium |
| Ir(ppz)$_3$: | tris(1-phenylpyrazoloto,N,C(2')iridium(III) |
| BCP: | 2,9-dimethyl-4,7-diphenyl-1,10-phenanthroline |
| TAZ: | 3-phenyl-4-(1'-naphthyl)-5-phenyl-1,2,4-triazole |
| CuPc: | copper phthalocyanine. |
| ITO: | indium tin oxide |
| NPD: | N,N'-diphenyl-N-N'-di(1-naphthyl)-benzidine |
| TPD: | N,N'-diphenyl-N,N'-di(3-toly)-benzidine |
| BAlq: | aluminum(III)bis(2-methyl-8-quinolinato)4-phenyl-phenolate |
| mCP: | 1,3-N,N-dicarbazole-benzene |
| DCM: | 4-(dicyanoethylene)-6-(4-dimethylaminostyryl-2-methyl)-4H-pyran |
| DMQA: | N,N'-dimethylquinacridone |
| PEDOT:PSS: | an aqueous dispersion of poly(3,4-ethylenedioxythiophene) with polystyrenesulfonate (PSS) |

Experimental

Specific representative embodiments of the invention will now be described, including how such embodiments may be made. It is understood that the specific methods, materials, conditions, process parameters, apparatus and the like do not necessarily limit the scope of the invention.

In Reaction A shown below, the ligands (III) can be prepared using the Suzuki method by combining the starting reagents represented by graphic formulae I and II. The substituted or unsubstituted phenylboronic acids represented by graphic formula I may be purchased commercially or prepared using standard techniques as described by the following review; *Chem. Rev.* 1995, 95, 2457–2483, which summarizes the palladium catalyzed cross-coupling reactions between organic halides and boronic acids. Compounds represented by graphic formula II, may also be purchased commercially or prepared by methods described in *J. Org. Chem.* 2002, 67, 238–241. In Reaction A compounds represented by graphic formula I are reacted with the appropriately substituted 2-chloro,bromo, or iodo substituted pyridines represented by graphic formula II and are combined in an appropriate solvent, e.g. dimethoxyethane (DME), xylenes. In addition, an aqueous base solution e.g., Na$_2$CO$_3$, K$_2$CO$_3$, K$_3$PO$_4$, a Palladium catalyst such as Pd(II) acetate, Pd(PPh$_3$)$_4$, and a reducing agent triphenylphosphine (TPP) if necessary is combined and refluxed until the reaction is completed. After purification using column chromatography, moderate to high yields are obtained to give the III as the final product.

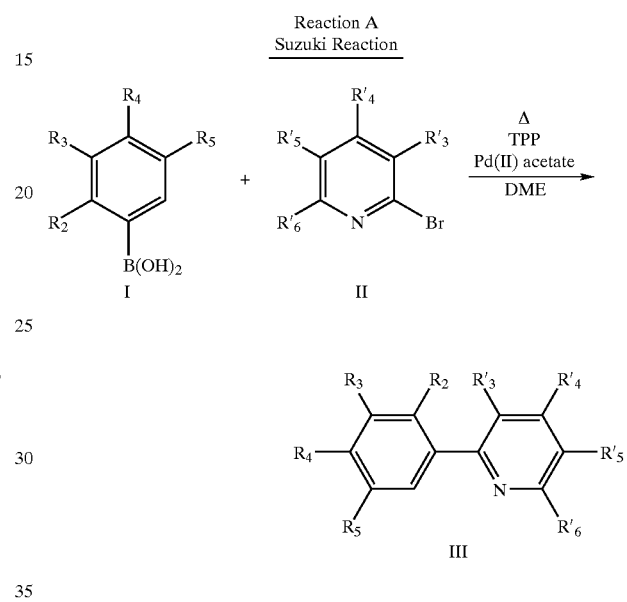

An alternate route to the desired substituted ligands (III) is to use the Stille reaction shown in Reaction C and described in the following *J. Org. Chem.* 2002, 67, 238–241 reference.

Those compounds represented by graphic formula IV can be found commercially available while heteroaromatic stannanes represented by graphic formula V can be prepared using following the methods described in *J. Org. Chem.* 2002, 67, 238–241 and depicted in Reaction B.

In Reaction B, a substituted pyridine is dissolved in a solvent under low temperatures followed by the addition of a base, e.g., butyl lithium, followed by the slow addition of the appropreiate electrophile,

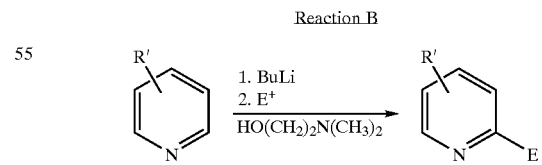

Compounds represented by graphic formulae IV and V shown below in Reaction C are combined in a solvent, e.g., xylenes, pyridine, toluene etc. and reacted in the presence of a Palladium (II) or Palladium (0) catalyst e.g., PdCl$_2$(PPh$_3$)$_2$, Pd(PPh$_3$)$_4$ and a reducing agent, PPh$_3$ if needed and reacted to give III. Purification of the crude ligand III is performed using standard techniques such as column chromatography or precipitation using common solvents

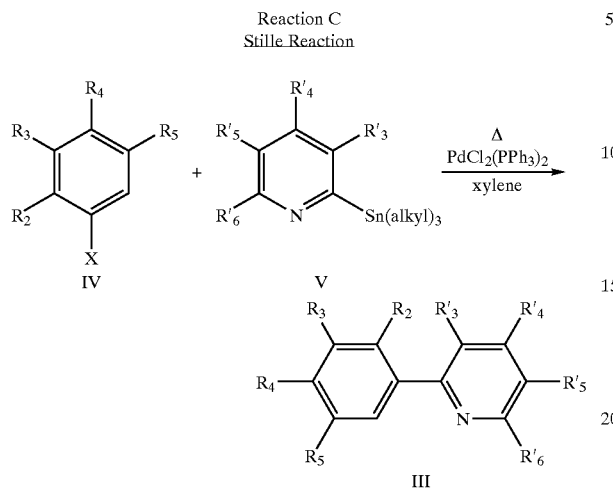

Reaction C
Stille Reaction

In Reaction D, the substituted 2-phenylpyridine ligands prepared from Reaction A or Reaction C and represented by graphic formula III, can be reacted with a variety of metals, e.g., iridium, platinum, in the presence of a solvent, e,g, 2-methoxyethanol or 2-ethoxyethanol and water under refluxing conditions to produce the dichloro-bridge dimmer represented by graphic formula VI. A solid precipitate that is formed upon completion of the reaction is collected by vacuum filtration techniques and further purified if necessary.

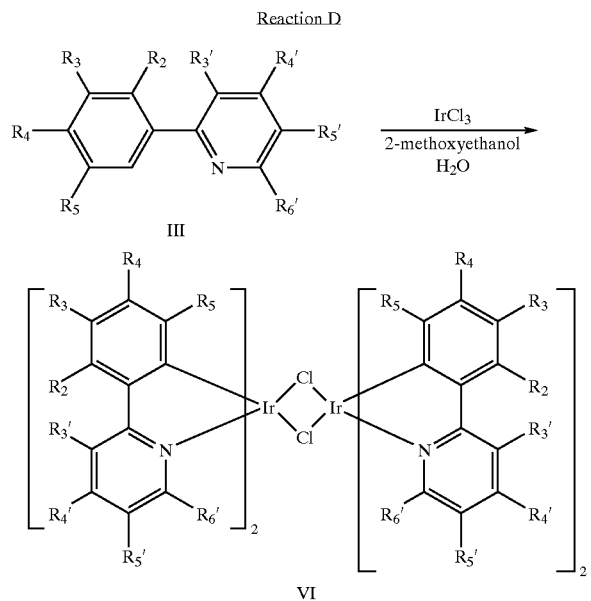

Reaction D

In Reaction E the dichlorobridge dimers represented by graphic formula VI can be reacted with a variety of monoanionic coordinating ligands, e.g. acetonacetyl (acac), picolinic acid, 4-dimethylaminopicolinic acid (DMAPic) and mono-anionic metal-carbon coordination ligands e.g., substituted 2-phenylpyridines, etc and is denoted by X and Y. The final isolated products represented by graphic VII are purified by standard techniques.

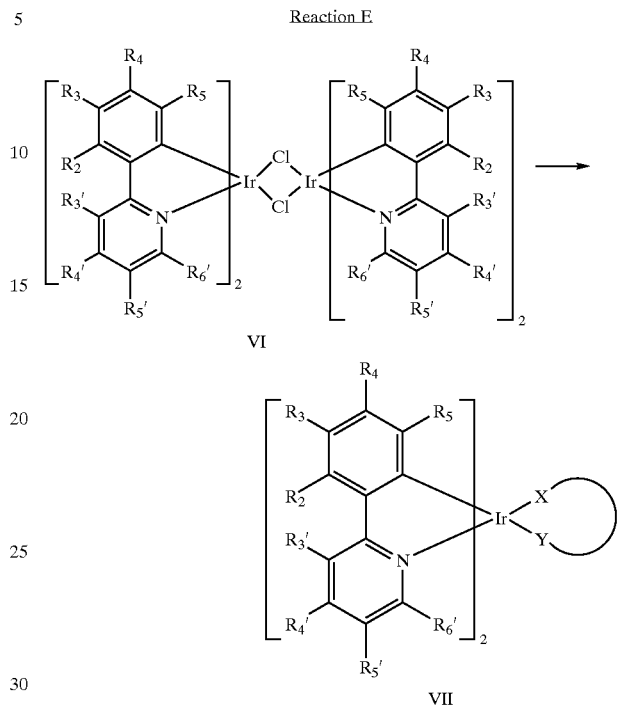

Comparative Example A

2-Bromopyridine (5.0 g 31.6 mmol), 2,4 difluoroboronic acid (6.0 g, 37.9 mmol) and triphenylphosphine (0.83g3.2 mmol) were dissolved in 50mL. of dimethoxyethane. To this mixture was added palladium acetate (0.18 g, 0.8 mmol) and 43 mL. of a 2M solution of potassium carbonate. The mixture was heated at reflux for 18 hours. The organic layer was separated and the aqueous layer was extracted three times with 125 mL. using ethyl acetate. The organic layers were combined and first washed with water followed by brine. The organic solvent was dried over magnesium sulfate, filtered and evaporated to leave an oil. The crude product was purified by column chromatography using silica gel and ethyl acetate and hexanes as the eluants. The fractions were collected and combined to give the desired product 2-(4,6-diflurophenyl)pyridine and was confirmed by NMR.

STEP 2: 2-(4,6-Difluorophenyl)pyridine (20.0 g 0.104 mol) from Step 1 above and iridium chloride hydrate (19.4 g, 0.052 mol) were added to 300 mL. of 2-ethoxyethanol and heated to reflux for 40 hours. The mixture was then cooled to room temperature, the crude dichlorobidged-dimer was vacuum filtered and washed with 2×150 mL. of 2-propanol. The crude dimer was then recrystallized and used in the following step.

STEP 3: Using a 500 ml flask 10.8 g (8.7 mmol) of the dimer, 2.1 g (17 mmol) of picolinic acid and 9.2 g (87 mmol) were added to 150 ml of 2-ethoxyethanol. This mixture was then heated at reflux for 18 hours. The mixture was then cooled to room temperature and vacuum filtered. The collected solid was added to 200 ml of deionized water and stirred at room temperature for one hour. This mixture was then vacuum filtered and washed with 100 mL. of ethanol and 100 mL. of hexanes. The collected product was then dried in a vacuum oven. Yield=11.6g. 95.8%.

EXAMPLE 1

STEP 1: 3,5-Bis(trifluoromethyl)phenylboronic acid (13.5 g, 52 mmol), 2-bromopyridine (6.2 g, 39 mmol), palladium (II) acetate (0.29 g, 1.3 mmol), triphenylphosphine (1.36 g, 5.2 mmol), and sodium carbonate (7 g, 68 mmol) were added to 200 mL. of 1,2-dimethoxyethane and 100 mL. of water. The reaction mixture was heated to reflux for 5 hours and after cooling, 100 mL of water and 100 mL. of ethyl acetate were added. The phases were separated, the organic layer was dried over magnesium sulfate and the excess solvent was removed. 2-(3,5-Bistrifluoromethylphenyl)pyridine was purified by column chromatography and collected as a white solid (7.1 g).

STEP 2: 2-(3,5-Bis(trifluoromethyl)phenyl)pyridine (1.4 g, 4.8 mmol) from Step 1 above and iridium (III) chloride hydrate (0.87 g, 2.4 mmol) were added to a flask containing 15 mL. of 2-methoxyethanol and 5 mL. of water. The reaction was heated to reflux for 16 hours and allowed to cool. The yellow precipitate that formed was collection by vacuum filtration. The crude dichloro-bridged dimer was not purified further but used directly as is.

STEP 3: The dichloro-bridged dimer (0.75 g 0.46 mmol) from Step 2 above was added to 50 mL. of 2-methoxyethanol. Sodium carbonate (0.48 g, 4.6 mmol) and 2,4-pentanedione (0.46 g, 4.6 mmol) were added to the reaction mixture. The reaction was heated to reflux for 16 hours. Water was added and the crude solid was collected through vacuum filtration and washed with ethanol and hexane. This material was purified by column chromatography and vacuum sublimation. NMR and Mass Spectroscopy results confirmed the desired compound.

EXAMPLE 3

STEP 1: 2,4-Difluoro-5-(trifluoromethyl)bromobenzene (2.0 g, 7.7 mmol), 2-tributylstannylpyridine, and Bis(triphenylphosphine)palladium(II)chloride (0.16 g, 0.23 mmol) were added to 50 mL. xylenes and the mixture was heated to reflux for 16 hours. The reaction mixture was filtered through a silica gel plug and then purified with column chromatography to give 2-(2,4-difluoro-5-trifluoromethylphenyl)pyridine (1.4 g, 5.4 mmol). The product was confirmed by Mass Spectroscopy and $^1$H NMR.

STEP 2: 2-(2,4-difuoro-5-trifuoromethylpenyl)pyridine (1.4 g, 5.4 mmol) and iridium (III) chloride hydrate (0.97 g, 2.7 mmol) were added to 10 mL. of 2-methoxyethanol and 3 mL. water. The reaction was heated for 16 hours and a light green precipitate was collected by vacuum filtration and washed with ethanol and hexanes. The dichloro-bridged dimer was dried in a vacuum oven to give 1.0 g (50% yield). The product was used directly in the next step without further purification.

STEP 3: The dichloro-bridged dimer (1.0 g, 0.65 mmol), sodium carbonate (1.34g, 13.4 mmol), and 2,4 pentanedione (1.3 g, 13.4 mmol) were added to 50 mL. of 2-methoxyethanol and heated to reflux for 16 hours. The reaction was cooled and then 50 mL. of water and 50 mL. dichloromethane were added. The phases separated and the organic was collected. The solvent was removed under vacuum and the product was purified by column chromatography followed by sublimation. $^1$H NMR and Mass Spectroscopy results confirmed the desired product.

Examples 2 and 5–12 were prepared by the Suzuki methods provide by Example 1 Step 1 followed by the synthesis of the dichloride-bridged dimers and appropriately substituted ancillary ligands.

Examples 3, 4, 13, 16 and 17 were prepared by the Stille methods provided by Example 3 Step 1 followed by the synthesis of the dichloride-bridged dimmer and appropriately substituted ancillary ligands.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art. CIE coordinates are described in H. Zollinger, "Color Chemistry" VCH Publishers, 1991 and H, J, A, Dartnall, J. K. Bowmaker, and J. D. Mollon, Proc. Roy. Soc. B (London), 1983, 220, 115–130, which are incorporated by reference. For example, the NTSC standard calls for a saturated blue having CIE (0.155, 0.07). The SRGB standard calls for CIE (0.15,0.06). Other industry standards may call for slightly different CIE coordinates.

Device fabrication

Devices 1, 3, 11, and Comparative Example A were fabricated by high vacuum (<10$^{-7}$ Torr) thermal evaporation. Indium tin oxide (ITO) anode on glass was used as the anode. The cathode consists of 10 Å of LiF followed by 1,000 Å of Al. All devices were encapsulated with a glass lid sealed with an epoxy resin in a nitrogen glove box (<1 ppm of H$_2$O and O$_2$) immediately after fabrication, and a moisture getter was incorporated inside the package. The CIE coordinates and maximum luminous efficiency (in cd/A) are summarized in following Table. For the examples without device efficiency, the CIE coordinates and emission maxima are obtained from the photoluminescence measured in CH$_2$Cl$_2$ solution.

TABLE 1

| Example | Device | M | R2 | R3 | R4 | R5 | R'4 | R'5 | R'6 | (X) Ligand | CIE coordinates | Emission (nm) | m | n | OLED max efficiency (cd/A) |
|---|---|---|---|---|---|---|---|---|---|---|---|---|---|---|---|
| A | A | Ir | H | H | H | H | H | H | H | AcAc | (0.33, 0.61) | 520 | 2 | 1 | 20 |
| 1 | 1 | Ir | H | CF3 | H | CF3 | H | H | H | AcAc | (0.19, 0.39) | 472 | 2 | 1 | 17 |
| 2 | | Ir | H | CF3 | H | CF3 | H | H | H | Pic | (0.19, 0.39) | 470 | 2 | 1 | |
| 3 | 3 | Ir | F | H | F | CF3 | H | H | H | AcAc | (0.17, 0.27) | 458 | 2 | 1 | 8.5 |
| 4 | | Ir | F | H | F | CF3 | H | H | H | Pic | (0.17, 0.31) | 457 | 2 | 1 | |
| 5 | | Ir | H | CF3 | H | CF3 | OCH3 | H | H | AcAc | (0.17, 0.37) | 468 | 2 | 1 | |
| 6 | | Ir | H | CF3 | H | CF3 | OCH3 | H | H | Pic | (0.18, 0.36) | 466 | 2 | 1 | |
| 7 | | Ir | H | CF3 | H | H | H | H | H | AcAc | (0.31, 0.53) | 510 | 2 | 1 | |

TABLE 1-continued

| Example | Device | M | R2 | R3 | R4 | R5 | R'4 | R'5 | R'6 | (X) Ligand | CIE coordinates | Emission (nm) | m | n | OLED max efficiency (cd/A) |
|---|---|---|---|---|---|---|---|---|---|---|---|---|---|---|---|
| 8 | | Ir | H | CF3 | H | H | H | H | H | Pic | (0.23, 0.51) | 484 | 2 | 1 | |
| 9 | | Ir | H | H | H | H | H | H | OCH3 | Pic | (0.34, 0.58) | 520 | 2 | 1 | |
| 10 | | Ir | H | CF3 | H | CF3 | N(CH3)2 | H | H | AcAc | (0.18, 0.31) | 463 | 2 | 1 | |
| 11 | 11 | Ir | H | CF3 | H | CF3 | pyrrolidon | H | H | AcAc | (0.18, 0.29) | 462 | 2 | 1 | 2.7 |
| 12 | | Ir | H | CF3 | H | CF3 | pyrrolidon | H | H | DMAPic | (0.21, 0.31) | 456 | 2 | 1 | |
| 13 | | Ir | F | H | F | CF3 | N(CH3)2 | H | H | DMAPic | (0.16, 0.22) | 450 | 2 | 1 | |
| 14 | | Ir | H | CN | H | H | H | H | H | AcAc | (0.26, 0.56) | 500 | 2 | 1 | |
| 15 | | Ir | H | CN | H | H | H | H | H | Pic | (0.22, 0.49) | 482 | 2 | 1 | |
| 16 | | Ir | F | H | H | CF3 | H | H | H | AcAc | (0.19, 0.35) | 468 | 2 | 1 | |
| 17 | | Ir | F | CN | F | H | H | H | H | Pic | 0.15, 0.38 | 452 | 2 | 1 | 11 |

COMPARATIVE EXAMPLE A

The organic stack consists of, from the anode to the cathode, 100 Å of copper phthalocyanine (CuPc), 300 Å of 4,4'-bis[N-(1-naphthyl)-N-phenylamino]biphenyl (α-NPD), 300 Å of 4,4'-bis(N-carbazolyl)biphenyl (CBP) doped with 6 wt % of Compound A as the emissive layer (EML), 100 Å of aluminum(III)bis(2-methyl-8-quinolinato)4-phenylphenolate (BAlq), and 400 Å of tris(8-hydroxyquinolinato)aluminum (Alq$_3$).

Device 1

The organic stack consists of, from the anode to the cathode, 100 Å of copper phthalocyanine (CuPc), 450 Å of 4,4'-bis[N-(1-naphthyl)-N-phenylamino]biphenyl (α-NPD), 300 Å of Compound B doped with 6 wt % of Compound 1 as the emissive layer (EML), and 400 Å of aluminum(III)bis(2-methyl-8-quinolinato)4-phenylphenolate (BAlq).

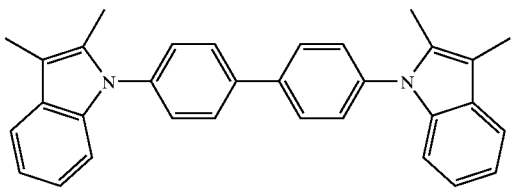

Compound B

Device 3

The organic stack consists of, from the anode to the cathode, 100 Å of copper phthalocyanine (CuPc), 450 Å of 4,4'-bis[N-(1-naphthyl)-N-phenylamino]biphenyl (α-NPD), 300 Å of Compound C doped with 6 wt % of Compound 3 as the emissive layer (EML), and 400 Å of aluminum(III) bis(2-methyl-8-quinolinato)4-phenylphenolate (BAlq)

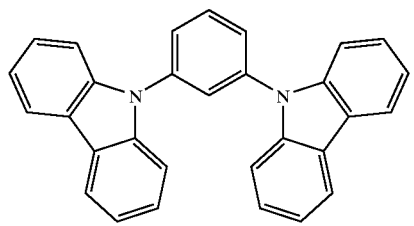

Compound C

Device 11

The organic stack consists of, from the anode to the cathode, 100 Å of copper phthalocyanine (CuPc), 300 Å of 4,4'-bis[N-(1-naphthyl)-N-phenylamino]biphenyl (α-NPD), 300 Å of Compound C doped with 6 wt % of Compound 11 as the emissive layer (EML), and 300 Å of aluminum(III) bis(2-methyl-8-quinolinato)4-phenylphenolate (BAlq).

Additional specific substituted FIrpic compounds were synthesized according to the following schemes: In Reaction F shown below, a compound represented by graphic formula X is prepared by combining the starting reagents represented by formulae VIII and IX. The substituted or unsubstituted phenylboronic acids represented by graphic formula VIII may be purchased commercially or prepared using standard techniques as described by the following review; Chem. Rev. 1995, 95, 2457–2483, which also summarizes the palladium catalyzed cross-coupling reactions between organic halides and boronic acids. Compounds represented by graphic formula IX, may also be purchased commercially or prepared by methods described in J. Org. Chem. 2002, 67, 238–241. In Reaction F compounds represented by graphic formula VIII are reacted with the appropriately substituted 2-chloro, bromo, or iodo pyridines represented by graphic formula IX and are combined in an appropriate solvent, e.g. dimethoxyethane (DME), xylenes. In addition, an aqueous base solution e.g., Na$_2$CO$_3$, K$_2$CO$_3$, K$_3$PO$_4$, a palladium catalyst such as Pd(II) acetate, Pd(PPh$_3$)$_4$, and a reducing agent triphenylphosphine (TPP) if necessary is combined and refluxed until the reaction is completed. After purification using column chromatography, moderate to high yields are obtained to give X.

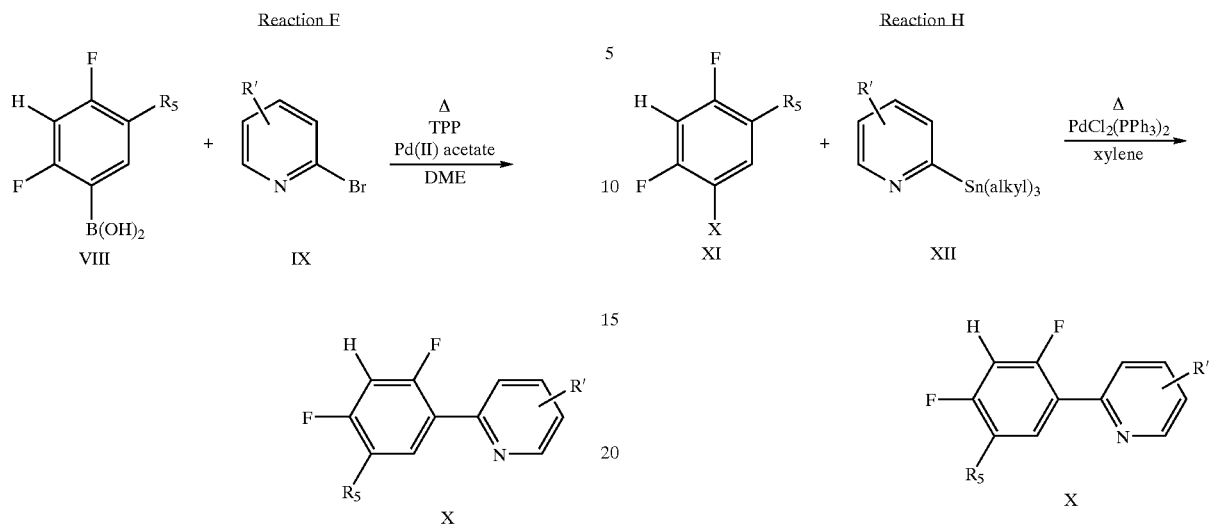

An alternate route to the desired substituted ligands (X) is shown in Reaction H and described in J. Org. Chem. 2002, 67, 238–241.

In Reaction H compounds represented by graphic formula XI where the X substituent is any halogen that can be prepared or are commercially available, the heteroaromatic stannanes represented by graphic formula XII can be prepared using following the methods described in J. Org. Chem. 2002, 67, 238–241 and depicted in Reaction G (shown below).

In Reaction G, a substituted pyridine is added to a mixture of. N,N-dimethylethanolamine (DMEA) and butyl lithium at low temperatures. This is followed by the slow addition of the appropriate electrophile, (E+) i.e. tributyl tin chloride, bromine, carbon tetrabromide etc. The crude products are purified using standard techniques such as column chromatography and recrystallization and can be used in Reaction F or Reaction H.

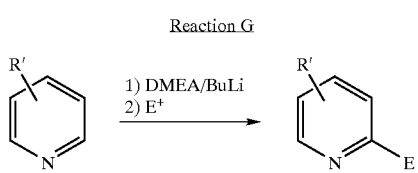

Compounds represented by graphic formulae XI and XII shown below in Reaction H are combined in a solvent, e.g., xylenes, pyridine, toluene and reacted in the presence of a Palladium (II) or Palladium (0) catalyst e.g., PdCl$_2$(PPh$_3$)$_2$, Pd(PPh$_3$)$_4$ and a reducing agent, PPh$_3$ if needed to give the desired ligand represented by graphic formula X. Purification of the crude ligand X is performed using standard techniques such as column chromatography or precipitation using common solvents.

In Reaction J below, a substituted or unsubstituted ligands are dissolved in anhydrous solvent i.e. THF to which a base i.e. LDA, is added at low temperatures. After addition of the base, an electrophile i.e, heptafluorobenzyl iodide is added. After the reaction is complete the crude material can be purified by standard conditions such as a silica gel to give the desired product represented by graphic formula XIII. Compound XIII is then reacted with the appropriate aryl or heteroaryl boronic acid in a similar manner described above in Reaction F to give compound XIV

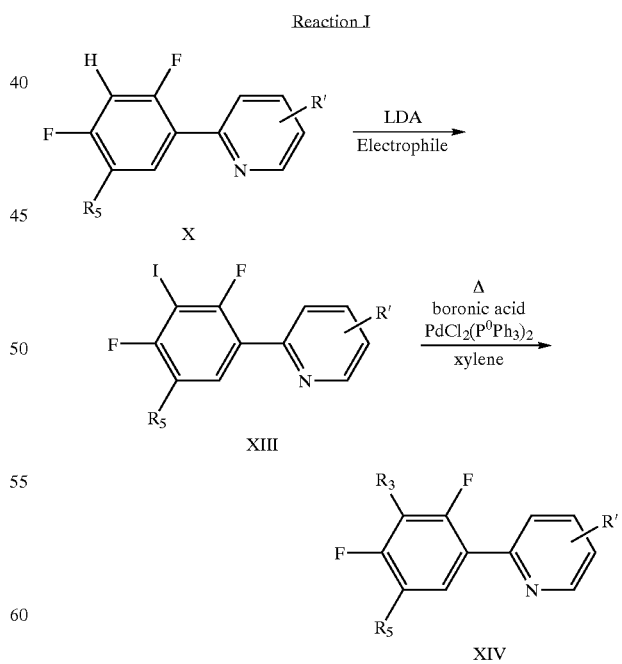

Alternatively, in Reaction K shown below, one could prepare compounds represented by graphic formula XIV where R3 is a cyano group by the following method. A compound represented by graphic formula XV shown in Reaction K below is reacted at low temperatures with an appropriate base such as lithium diisopropyl amide (LDA) and quenched with carbon dioxide (CO2). Compound XVI is reacted with thionyl chloride and ammonium hydroxide to give X as the carboxamide. Compound XVII is then reacted under dehydrating conditions i.e. acid (H+) to give XVIII. The compound represented by graphic formula XVIII is then converted to the photoactive ligand by replacing XVIII for XI in Reaction H to give III where R3 is now substituted with a cyano substituent.

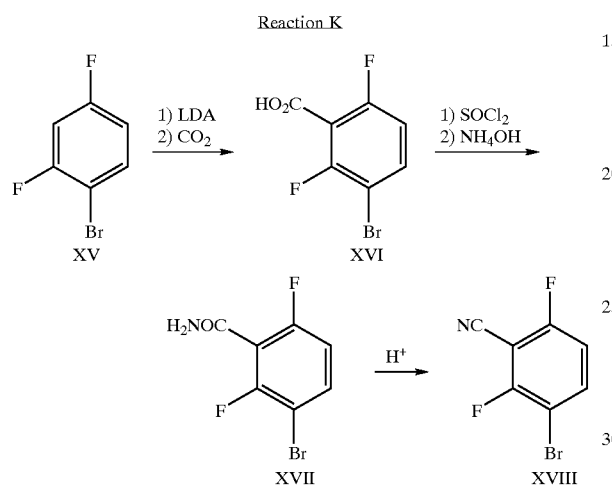

In Reaction L, the substituted or unsubstituted photoactive ligands prepared from Reaction J represented by graphic formula XIV, can be reacted with a variety of metals, e.g., iridium, platinum, in the presence of a solvent, e.g., 2-methoxyethanol or 2-ethoxyethanol and water under refluxing conditions to produce the dichloro-bridge dimer represented by graphic formula XIX. A solid precipitate that is formed upon completion of the reaction is collected by vacuum filtration techniques and further purified if necessary.

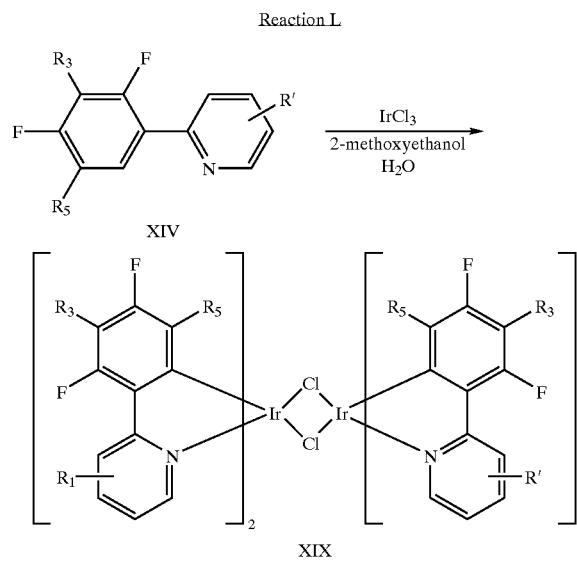

In Reaction M the dichloro-bridge dimers represented by graphic formula XIX can be reacted with a variety of mono-anionic coordinating ligands, e.g. acetonacetyl (acac), picolinic acid, 4-dimethylaminopicolinic acid (DMAPic) and is denoted by X and Y. The final isolated products represented by graphic XX are purified by standard techniques.

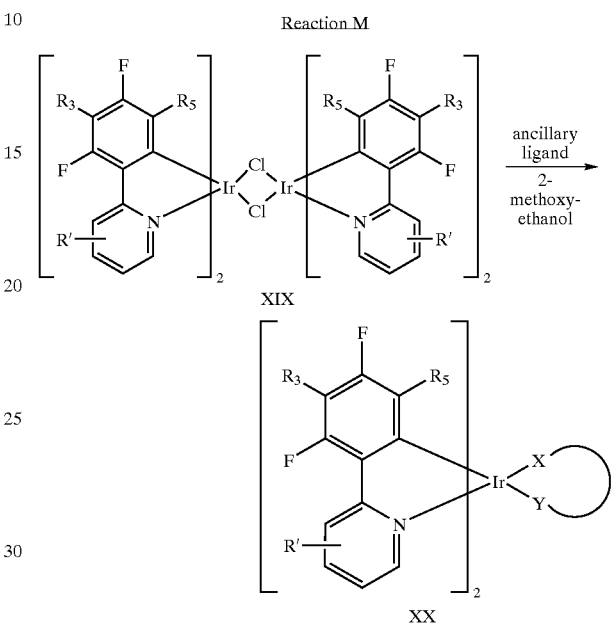

Each of the materials in Table 2 was synthesized. Each material had the structure illustrated by Formula 2, where M=Ir, and $R_5 \leq R'$=H. Except for entries 18 and 29, each of the materials had m=2, with one ancillary ligand (n=1) as indicated. Entries 18 and 29 had m=3, as indicated by the "tris" entry in the ancillary column, such that there was no ancillary ligand. Entries 19 and 21 were synthesized in accordance with the examples provided above. The other entries were synthesized using similar techniques apparent to one of skill in the art in view of the examples provided above. A small amount of each material was dissolved in dichloromethane. Each solution was optically pumped, and the resultant photoluminescent spectra were measured. The resultant peak wavelengths and CIE coordinates are tabulated in Table 2. Hammett values for the $R_3$ substituent in the para position (σ para) were drawn from the literature for compounds 1 σ para for Ph=−0.01), and compounds 10 and 11 (σ para for CN=0.66)

TABLE 2

| Compound | Device | $R_3$ | ancillary ligand | Peak emission (nm) | PL CIE | OLED maximum efficiency (cd/A) |
|---|---|---|---|---|---|---|
| 18 | 31 | CO$_2$Me | none (tris) | 460 | 0.16, 0.29 | 14 |
| 19 | 19 | Ph | pic | 474 | 0.17, 0.38 | 12 |
| 20 | | 4-CF$_3$Ph | pic | 470 | 0.16, 0.33 | |
| 21 | | 2-pyridine | acac | 482 | 0.17, 0.45 | |
| 22 | | 2-pyridine | pic | 468 | 0.17, 0.34 | |
| 23 | | 2-pyrimidine | acac | 484 | 0.18, 0.46 | |
| 24 | | 2-pyrimidine | pic | 467 | 0.17, 0.33 | |

TABLE 2-continued

| Compound | Device | R₃ | ancillary ligand | Peak emission (nm) | PL CIE | OLED maximum efficiency (cd/A) |
|---|---|---|---|---|---|---|
| 25 | | 4-pyridine | acac | 480 | 0.15, 0.39 | |
| 26 | | 4-pyridine | pic | 468 | 0.17, 0.33 | |
| 27 | | 3-pyridine | pic | 470 | 0.17, 0.33 | |
| 28 | 28 | CN | pic | 452 | 0.15, 0.19 | 11 |
| 29 | 29 | CN | none (tris) | 450 | 0.17, 0.19 | 7 |
| 30 (FIrpic) | 30 | H | pic | 468 | 0.17, 0.32 | 12 |

Device Fabrication

Devices 18, 19, 28, 29, and 30 were fabricated by high vacuum (<10⁻⁷ Torr) thermal evaporation. Indium tin oxide (ITO) anode on glass was used as the anode. The cathode consists of 10 Å of LiF followed by 1,000 Å of Al. All devices were encapsulated with a glass lid sealed with an epoxy resin in a nitrogen glove box (<1 ppm of H₂O and O₂) immediately after fabrication, and a moisture getter was incorporated inside the package. The CIE coordinates and maximum luminous efficiency (in cd/A) are summarized in Table 2. The CIE coordinates and emission maxima are obtained from the photoluminescence measured in CH₂Cl₂ solution.

Device 18

The organic stack consists of, from the anode to the cathode, 100 Å of copper phthalocyanine (CuPc), 300 Å of 4,4'-bis[N-(1-naphthyl)-N-phenylamino]biphenyl (α-NPD), 300 Å of Compound C doped with 6 wt % of Compound 31 as the emissive layer (EML), 400 Å aluminum(III)bis(2-methyl-8-quinolinato)4-phenylphenolate (BAlq).

Device 19

The organic stack consists of, from the anode to the cathode, 100 Å of copper phthalocyanine (CuPc), 300 Å of 4,4'-bis[N-(1-naphthyl)-N-phenylamino]biphenyl (α-NPD), 300 Å of 4,4'-bis(N-carbazolyl)biphenyl (CBP) doped with 6 wt % of Compound 19 as the emissive layer (EML), 400 Å of aluminum(III)bis(2-methyl-8-quinolinato)4-phenylphenolate (BAlq).

Device 28

The organic stack consists of, from the anode to the cathode, 100 Å of copper phthalocyanine (CuPc), 450 Å of 4,4'-bis[N-(1-naphthyl)-N-phenylamino]biphenyl (α-NPD), 300 Å of compound C doped with 6 wt % of Compound 28 as the emissive layer (EML), and 400 Å of aluminum(III)bis(2-methyl-8-quinolinato)4-phenylphenolate (BAlq).

Device 29

The organic stack consists of, from the anode to the cathode, 100 Å of copper phthalocyanine (CuPc), 450 Å of 4,4'-bis[N-(1-naphthyl)-N-phenylamino]biphenyl (α-NPD), 300 Å of Compound C doped with 6 wt % of Compound 29 as the emissive layer (EML), and 400 Å of aluminum(III)bis(2-methyl-8-quinolinato)4-phenylphenolate (BAlq).

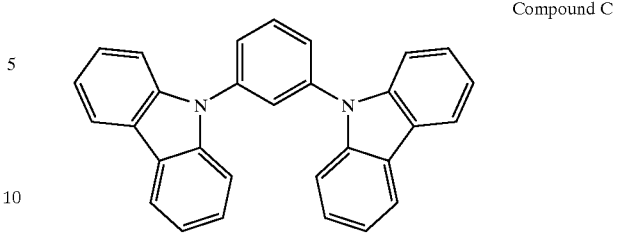

Compound C

Device 30

The organic stack consists of, from the anode to the cathode, 100 Å of copper phthalocyanine (CuPc), 300 Å of 4,4'-bis[N-(1-naphthyl)-N-phenylamino]biphenyl (α-NPD), 300 Å of 4,4'-bis(N-carbazolyl)biphenyl (CBP) doped with 6 wt % of Compound 30 as the emissive layer (EML), 400 Å of aluminum(III)bis(2-methyl-8-quinolinato)4-phenylphenolate (BAlq).

Compounds 19 and 28 from Table 2, and FIrpic were further characterized for stability. (Compound 28 is identical to compound 17 in Table 1). The photoluminescent stability (PL) testing system used to test these samples monitors PL emission of a sample under UV excitation as a function of time. The system uses a mercury-xenon (Hg—Xe) UV lamp to excite a thin film sample on a quartz substrate. The broad UV emission of the lamp is delivered to the sample through a narrow band UV filter, which selects the 313nm Hg line. During testing, the sample is kept under high vacuum (<5×10⁻⁷ Torr). Silicon diode photodetectors monitor the emission intensities of the thin film sample and the lamp.

Host and dopant were co-evaporated in a vacuum chamber (<5×10⁻⁸ Torr) from different sources to form a thin film of 50 nm thickness on a quartz substrate. The dopant was present in a concentration of 6 wt %. The host deposition rate was 1.6 Å/s. Next, the sample was exposed to atmospheric pressure in an inert nitrogen ambient (<1 ppm O₂ and H₂O), where the sample was placed in the PL testing system vacuum chamber and subsequently evacuated to <1×10⁻⁶ Torr. Next, the sample was exposed to 313nm UV radiation at a power density of 0.6 mW/cm2, resulting in a PL intensity of at least 20 cd/m2, and its photoluminescence intensity was recorded as a function of time. Also, the UV source intensity was recorded as a function of time.

Figure 3:
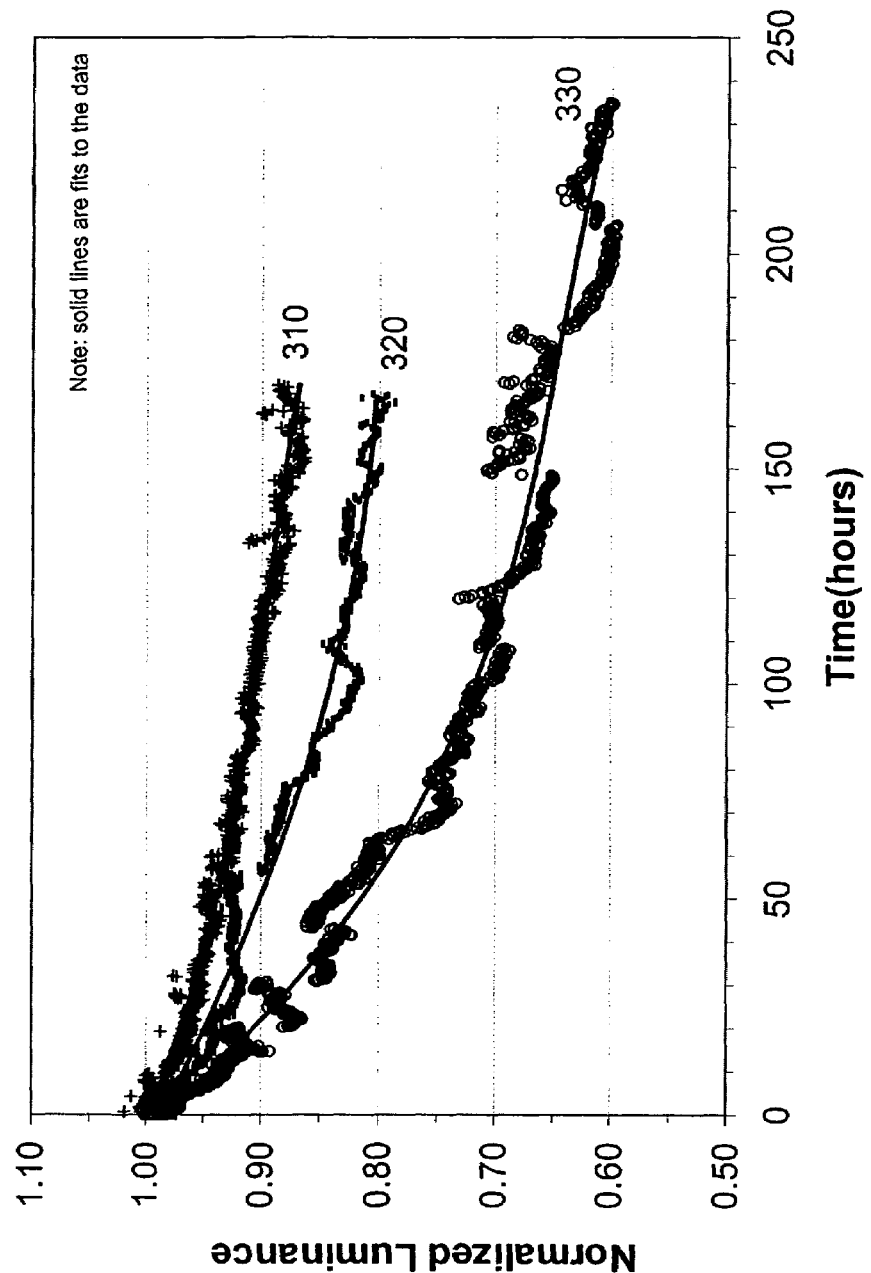
FIG. 3 shows stability plots for various materials.

Three samples were prepared. Sample 1 was Compound 19 doped into CBP. Sample 2 was compound 28 doped into Compound C. Sample 3 was FIrpic doped into CBP. The host materials were selected based on energy transfer considerations, and it is not expected that the differences in host material will significantly affect photoluminescent lifetime testing results. Each thin film was optically pumped, and the photoluminescent intensity was measured as a function of time. The initial PL intensity was about 20 cd/m2. The results are plotted in FIG. 3. Plots 310, 320 and 330 show the photoluminescent intensities of the compound 19, compound 28, and FIrpic films, respectively. $L_{100}/L_0$ values, which indicate the intensity at 100 hours as a percentage of the intensity at zero hours, were also determined for each material. The $L_{100}/L_0$ values for compound 19, compound 28, and FIrpic were 91%, 82% and 71%, respectively. The plots of FIG. 3, as well as the $L_{100}/L_0$ values, demonstrate that compound 19 and compound 28 are more stable than FIrpic, and demonstrate the more general principal that providing a substituent in the R3 position increases stability. These results show that some embodiments of the present invention have emission characteristics similar to FIrpic, or even closer to saturated blue than FIrpic, and with enhanced stability. Notably, compound 28 has a CIE "distance" of about 0.12 from saturated blue.

While the present invention is described with respect to particular examples and preferred embodiments, it is understood that the present invention is not limited to these examples and embodiments. The present invention as claimed therefore includes variations from the particular examples and preferred embodiments described herein, as will be apparent to one of skill in the art.

The invention claimed is:

1. An emissive material represented by the structure:

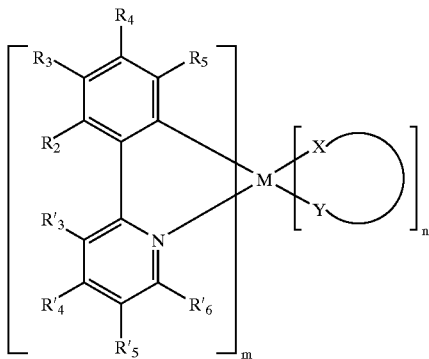

wherein M is a heavy metal with an atomic weight of greater than or equal to 40;

$R_3$ is a substituent having a Hammett value greater than 0.6;

each of $R_2$, $R_4$, $R_5$, and $R'_3$ through $R'_6$ are independently selected from the group consisting of H, halogens, CN, perfluoroalkyl, trifluorovinyl, $NO_2$, $CO_2R$, $C(O)R$, $S(O)R$, $SO_2R$, $SO_3R$, $P(O)R$, $PO_2R$, $PO_3R$, $C\equiv CR$, alkyl, alkenyl, aryl, heteroaryl, OR, SR, $NR_2$ (including cyclic-amino), and $PR_2$ (including cyclic-phosphino), where R is hydrogen, an alkyl group, an aryl group or a heteroaryl group;

m is an integer between 1 and 4 and n is an integer between 1 and 3; and,

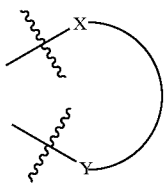

is a monoanionic non carbon coordinating ligand.

2. The emissive material of claim 1 wherein $R_4$ is H.

3. The emissive material of claim 1 wherein $R_5$ is an electron withdrawing group.

4. The emissive material of claim 1 wherein at least one of $R_2$ and $R_4$ is an electron withdrawing group.

5. The emissive material of claim 3 wherein at least one of $R_2$ and $R_4$ is an electron withdrawing group.

6. The emissive material of claim 1 wherein at least one substituent of the emissive material is an electron withdrawing group selected from halogens, CN, perfluoroalkyl, trifluorovinyl, $NO_2$, $CO_2R$, $C(O)R$, $S(O)R$, $SO_2R$, $SO_3R$, $P(O)R$, $PO_2R$, $PO_3R$, $C\equiv CR$, and aryl and heteroaryl groups substituted with halogens, CN, perfluoroalkyl, trifluorovinyl, $NO_2$, $CO_2R$, $C(O)R$, $S(O)R$, $SO_2R$, $SO_3R$, $P(O)R$, $PO_2R$, or $PO_3R$, where R is a hydrogen, alkyl, aryl or heteroaryl group.

7. The emissive material of claim 1 wherein $R_5$ is an electron donating group.

8. The emissive material of claim 1 wherein at least one substituent of the emissive material is an electron donating group selected from alkyl, alkenyl, aryl, heteroaryl, OR, SR, $NR_2$ (including cyclic-amino), and $PR_2$ (including cyclic-phosphino), where R is a hydrogen, alkyl, aryl or heteroaryl group.

9. The emissive material of claim 1 wherein the metal is selected from Ir, Pt, Pd, Rh, Re, Os, Tl, Pb, Bi, In, Sn, Sb, Te, Au, and Ag.

10. The emissive material of claim 1 wherein the metal is iridium.

11. The emissive material of claim 1 wherein the metal is platinum.

12. A composition represented by the structure:

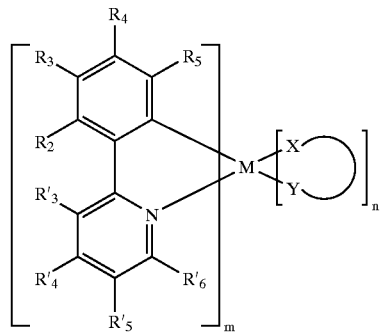

wherein M is a heavy metal with an atomic weight of greater than or equal to 40;

each of $R_2$ through $R_5$ and $R'_3$ through $R'_6$ are independently selected from the group consisting of H, halogens, CN, perfluoroalkyl, trifluorovinyl, $NO_2$, $CO_2R$, $C(O)R$, $S(O)R$, $SO_2R$, $SO_3R$, $P(O)R$, $PO_2R$, $PO_3R$, $C\equiv CR$, alkyl, alkenyl, aryl, heteroaryl, OR, SR, $NR_2$ (including cyclic-amino), and $PR_2$ (including cyclic-phosphino), where R is hydrogen, an alkyl group, an aryl group or a heteroaryl group, wherein at least one of $R_3$ and $R_5$ is CN;

m is an integer between 1 and 4 and n is an integer between 1 and 3;

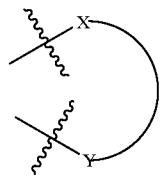

is a monoanionic non carbon coordinating ligand; and, wherein if neither $R_3$ nor $R_5$ is an electron donating group then $R'_4$ is an electron donating group.

13. The composition of claim 12, wherein neither $R_3$ nor $R_5$ is an electron donating group and wherein $R'_4$ is an electron donating group.

14. The composition of claim 12, wherein R'$_4$ is an electron donating group.

15. The composition of claim 12, wherein one of R$_3$ and R$_5$ is an electron donating group, and R'$_4$ is an electron withdrawing group.

16. The composition of claim 12 wherein at least one substituent of the composition is an electron withdrawing group selected from halogens, perfluoroalkyl, trifluorovinyl, NO$_2$, CO$_2$R, C(O)R, S(O)R, SO$_2$R, SO$_3$R, P(O)R, PO$_2$R, PO$_3$R, C≡CR, and aryl and heteroaryl groups substituted with halogens, CN, perfluoroalkyl, trifluorovinyl, NO$_2$, CO$_2$R, C(O)R, S(O)R, SO$_2$R, SO$_3$R, P(O)R, PO$_2$R, or PO$_3$R, where R is a hydrogen, alkyl, aryl or heteroaryl group.

17. The composition of claim 12 wherein at least one substituent of the composition is an electron donating group selected from alkyl, alkenyl, aryl, heteroaryl, OR, SR, NR$_2$ (including cyclic-amino), and PR$_2$ (including cyclic-phosphino), where R is a hydrogen, alkyl, aryl or heteroaryl group.

18. The composition of claim 12 wherein the metal is selected from Ir, Pt, Pd, Rh, Re, Os, Tl, Pb, Bi, In, Sn, Sb, Te, Au, and Ag.

19. A composition represented by the structure:

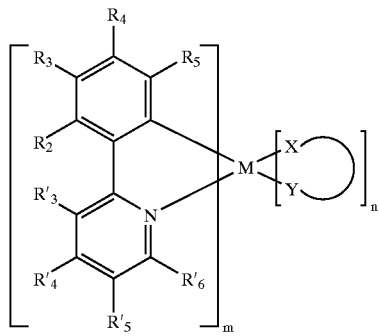

wherein M is a heavy metal with an atomic weight of greater than or equal to 40;

each of R$_2$, R$_4$, and R'$_3$ through R'$_6$ are independently selected from the group consisting of H, halogens, CN, perfluoroalkyl, trifluorovinyl, NO$_2$, CO$_2$R, C(O)R, S(O)R, SO$_2$R, SO$_3$R, P(O)R, PO$_2$R, PO$_3$R, C≡CR, alkyl, alkenyl, aryl, heteroaryl, OR, SR, NR$_2$ (including cyclic-amino), and PR$_2$ (including cyclic-phosphino), where R is hydrogen, an alkyl group, an aryl group or a heteroaryl group;

at least one of R$_3$ and R$_5$ is CN, and, where only one of R$_3$ and R$_5$ is CN, the other is selected from the group consisting of H, perfluoroalkyl, trifluorovinyl, NO$_2$, CO$_2$R, C(O)R, S(O)R, SO$_2$R, SO$_3$R, P(O)R, PO$_2$R, PO$_3$R, C≡CR, and aryl and heteroaryl groups substituted with halogens, CN, perfluoroalkyl, trifluorovinyl, NO$_2$, CO$_2$R, C(O)R, S(O)R, SO$_2$R, SO$_3$R, P(O)R, PO$_2$R, or PO$_3$R, where R is a hydrogen, alkyl, aryl or heteroaryl group, wherein m is an integer between 1 and 4 and n is an integer between 1 and 3 and X-Y is non carbon coordinating monoamonic ligand.

20. The composition of claim 19 wherein at least one of R$_2$ and R$_4$ is F.

21. The composition of claim 20 wherein R'$_4$ is an electron donating group.

22. The composition of claim 20 wherein R'$_4$ is NMe$_2$.

23. The composition of claim 19 wherein one of R$_3$ and R$_5$ is CF$_3$.

24. The composition of claim 23 wherein at least one of R$_2$ and R$_4$ is F.

25. The composition of claim 23 wherein R'$_4$ is an electron donating group.

26. The composition of claim 23 wherein R'$_4$ is NMe$_2$.

27. A light emitting device comprising an organic layer, the organic layer comprising a composition represented by the structure:

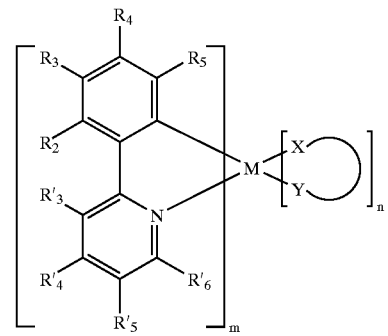

wherein M is a heavy metal with an atomic weight of greater than or equal to 40;

each of R$_2$ through R$_5$ and R'$_3$ through R'$_6$ are independently selected from the group consisting of H, halogens, CN, perfluoroalkyl, trifluorovinyl, NO$_2$, CO$_2$R, C(O)R, S(O)R, SO$_2$R, SO$_3$R, P(O)R, PO$_2$R, PO$_3$R, C≡CR, alkyl, alkenyl, aryl, heteroaryl, OR, SR, NR$_2$ (including cyclic-amino), and PR$_2$ (including cyclic-phosphino), where R is hydrogen, an alkyl group, an aryl group or a heteroaryl group, wherein at least one of R$_3$ and R$_5$ is CN;

one of R$_3$ and R$_5$ is optionally an electron donating group;

m is an integer between 1 and 4 and n is an integer between 1 and 3: and

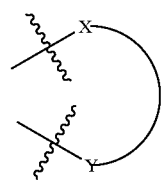

is a monoanionic non carbon coordinating ligand.

28. The light emitting device of claim 27 wherein R$_3$ and R$_5$ are both electron withdrawing groups.

29. The light emitting device of claim 27 wherein R$_3$ is an electron withdrawing group.

30. The light emitting device of claim 29 wherein R$_2$ and R$_4$ are electron withdrawing groups.

31. The light emitting device of claim 27 wherein R$_2$ and R$_4$ are electron withdrawing groups.

32. The light emitting device of claim 27 wherein one of R$_3$ and R$_5$ is an electron donating group.

33. The light emitting device of claim 27 wherein at least one substituent of the emissive material is an electron donating group selected from alkyl, alkenyl, aryl, heteroaryl, OR, SR, NR$_2$ (including cyclic-amino), and PR$_2$ (including cyclic-phosphino), where R is a hydrogen, alkyl, aryl or heteroaryl group.

34. The light emitting device of claim 27 wherein the metal is selected from Ir, Pt, Pd, Rh, Re, Os, Tl, Pb, Bi, In, Sn, Sb, Te, Au, and Ag.

35. The light emitting device of claim 27 wherein the metal is Pt.

36. The light emitting device of claim 27 wherein the metal is Ir.

37. The light emitting device of claim 27 wherein light emitted by the organic layer has a maximum wavelength of less than 520 nm.

38. The light emitting device of claim 27 wherein light emitted by the organic layer has a wavelength of between approximately 420 nm and approximately 480 nm.

39. A light emitting device comprising an organic layer, the organic layer comprising a composition represented by the structure:

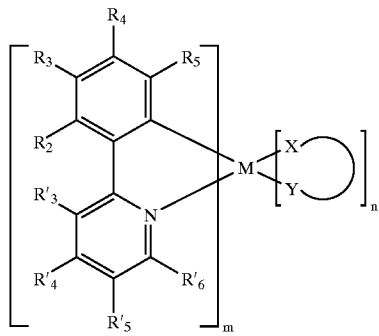

wherein M is a heavy metal with an atomic weight of greater than or equal to 40;
each of R$_2$ through R$_5$ and R'$_3$ through R'$_6$ are independently selected from the group consisting of H, halogens, CN, perfluoroalkyl, trifluorovinyl, NO$_2$, CO$_2$R, C(O)R, S(O)R, SO$_2$R, SO$_3$R, P(O)R, PO$_2$R, PO$_3$R, C≡CR, alkyl, alkenyl, aryl, heteroaryl, OR, SR, NR$_2$ (including cyclic-amino), and PR$_2$ (including cyclic-phosphino), where R is hydrogen, an alkyl group, an aryl group or a heteroaryl group, wherein at least one of R$_3$ and R$_5$ is CN;
one of R$_3$ and R$_5$ is optionally an electron donating group;
m is an integer between 1 and 4 and n is an integer between 1 and 3;

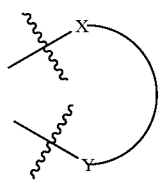

is a monoanionic non carbon coordinated ligand; and,
wherein if neither R$_3$ nor R$_5$ is an electron donating group then R'$_4$ is an electron donating group.

40. The light emitting device of claim 39, wherein R'$_4$ is an electron donating group.

41. The light emitting device of claim 39, wherein both R$_3$ and R$_5$ are electron withdrawing groups and R'$_4$ is an electron donating group.

42. The light emitting device of claim 39, wherein one of R$_3$ and R$_5$ is an electron donating group and R'$_4$ is an electron withdrawing group.

43. The light emitting device of claim 39, wherein R'$_4$ is an electron withdrawing group.

44. The light emitting device of claim 39 wherein at least one substituent of the composition is an electron withdrawing group selected from halogens, perfluoroalkyl, trifluorovinyl, NO$_2$, CO$_2$R, C(O)R, S(O)R, SO$_2$R, SO$_3$R, P(O)R, PO$_2$R, PO$_3$R, C≡CR, and aryl and heteroaryl groups substituted with halogens, CN, perfluoroalkyl, trifluorovinyl, NO$_2$, CO$_2$R, C(O)R, S(O)R, SO$_2$R, SO$_3$R, P(O)R, PO$_2$R, or PO$_3$R, where R is a hydrogen, alkyl, aryl or heteroaryl group.

45. The light emitting device of claim 39 wherein at least one substituent of the composition is an electron donating group selected from alkyl, alkenyl, aryl, heteroaryl, OR, SR, NR$_2$ (including cyclic-amino), and PR$_2$ (including cyclic-phosphino), where R is a hydrogen, alkyl, aryl or heteroaryl group.

46. The light emitting device of claim 39 wherein the metal is selected from Ir, Pt, Pd, Rh, Re, Os, Tl, Pb, Bi, In, Sn, Sb, Te, Au, and Ag.

47. The light emitting device of claim 39 wherein the metal is Pt.

48. The light emitting device of claim 39 wherein the metal is Ir.

49. The light emitting device of claim 39, wherein light emitted by the organic layer has a maximum wavelength of less than 520 nm.

50. The light emitting device of claim 39 wherein light emitted by the organic layer has a wavelength of between approximately 420 nm and approximately 480 nm.

51. A light emitting device comprising an organic layer, the organic layer comprising a composition represented by the structure:

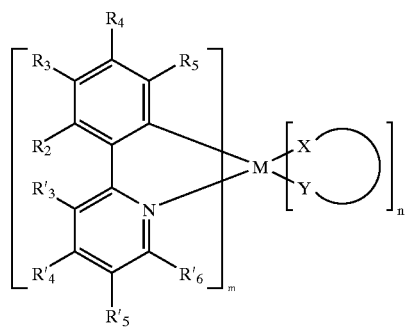

wherein M is a heavy metal with an atomic weight of greater than or equal to 40;
each of R$_2$, R$_4$, and R'$_3$ through R'$_6$ are independently selected from the group consisting of H, halogens, CN, perfluoroalkyl, trifluorovinyl, NO$_2$, CO$_2$R, C(O)R, S(O)R, SO$_2$R, SO$_3$R, P(O)R, PO$_2$R, PO$_3$R, C≡CR, alkyl, alkenyl, aryl, heteroaryl, OR, SR, NR$_2$ (including cyclic-amino), and PR$_2$ (including cyclic-phosphino), where R is hydrogen, an ailcyl group, an aryl group or a heteroaryl group;
m is an integer between 1 and 4 and n is an integer between 1 and 3; and,

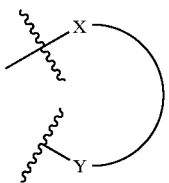

is a monoanionic non carbon coordinating ligand;
at least one of $R_3$ and $R_5$ is CN, and where only one of $R_3$ and $R_5$ is CN, the other is selected from the group consisting of H, perfluoroalkyl, trifluorovinyl, $NO_2$, $CO_2R$, C(O)R, S(O)R, $SO_2R$, $SO_3R$, P(O)R, $PO_2R$, $PO_3R$, C≡CR, and aryl and heteroaryl groups substituted with halogens, CN, perfluoroalkyl, trifluorovinyl, $NO_2$, $CO_2R$, C(O)R, S(O)R, $SO_2R$, $SO_3R$, P(O)R, $PO_2R$, or $PO_3R$, where R is a hydrogen, alkyl, aryl or heteroaryl group.

52. The light emitting device of claim 51 wherein at least one of $R_2$ and $R_4$ is F.

53. The light emitting device of claim 51 wherein one of $R_3$ and $R_5$ is $CF_3$.

54. The light emitting device of claim 51 wherein one of $R_3$ and $R_5$ is $CF_3$, and at least one of $R_2$ and $R_4$ is F.

55. A composition represented by the following structure:

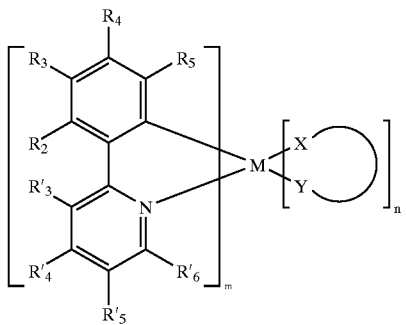

wherein M is a heavy metal with an atomic weight of greater than or equal to 40;
each of $R_2$ through $R_5$ and $R'_3$ through $R'_6$ are independently selected from the group consisting of H, halogens, CN, perfluoroalkyl, trifluorovinyl, $NO_2$, $CO_2R$, C(O)R, S(O)R, $SO_2R$, $SO_3R$, P(O)R, $PO_2R$, $PO_3R$, C≡CR, alkyl, alkenyl, aryl, heteroaryl, OR, SR, $NR_2$ (including cyclic-amino), and $PR_2$ (including cyclic-phosphino), where R is hydrogen, an alkyl group, an aryl group or a heteroaryl group, wherein at least one of $R_3$ and $R_5$ is CN;
m is an integer between 1 and 4 and n is an integer between 1 and 3; and,

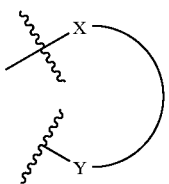

is a monoanionic non carbon coordinating ligand,
wherein $R_3$ and $R_5$ are selected to provide a hypsochromic shift in the emission spectrum of the compound of greater than or equal to approximately 40 nm as compared with the emission spectrum of a composition with the following structure:

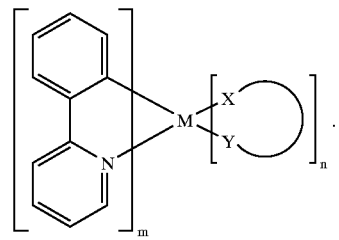

56. An emissive material represented by the structure:

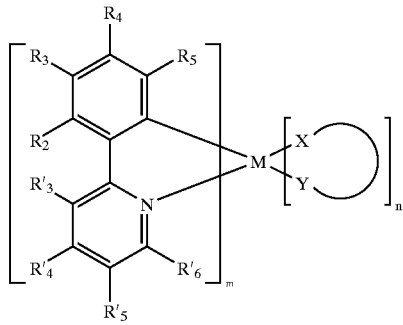

wherein M is a heavy metal with an atomic weight of greater than or equal to 40; m is at least 1 n is at least 0
X-Y is an ancillary ligand;
$R_2$ and $R_4$ are both F;
each of $R_3$, $R_5$, and $R'_3$ through $R'_6$ are independently selected from the group consisting of H, halogens, CN, perfluoroalkyl, trifluorovinyl, $NO_2$, $CO_2R$, C(O)R, S(O)R, $SO_2R$, $SO_3R$, P(O)R, $PO_2R$, $PO_3R$, C≡CR, alkyl, alkenyl, aryl, heteroaryl, OR, SR, $NR_2$ (including cyclic-amino), and $PR_2$ (including cyclic-phosphino), where R is hydrogen, an alkyl group, an aryl group or a heteroaryl group, wherein at least one of $R_3$ and $R_5$ is CN.

57. The emissive material of claim 56 wherein $R_3$ and $R_5$ are both electron withdrawing groups.

58. The emissive material of claim 56 wherein $R_3$ is an electron withdrawing group.

59. The emissive material of claim 56 wherein at least one substituent of the emissive material is an electron withdrawing group selected from halogens, perfluoroalkyl, trifluorovinyl, $NO_2$, $CO_2R$, C(O)R, S(O)R, $SO_2R$, $SO_3R$, P(O)R, $PO_2R$, $PO_3R$, C≡CR, and aryl and heteroaryl groups substituted with halogens, CN, perfluoroalkyl, trifluorovinyl, $NO_2$, $CO_2R$, C(O)R, S(O)R, $SO_2R$, $SO_3R$, P(O)R, $PO_2R$, or $PO_3R$, where R is a hydrogen, alkyl, aryl or heteroaryl group.

60. The emissive material of claim 56 wherein one of $R_3$ and $R_5$ is an electron donating group.

61. The emissive material of claim 56 wherein $R_3$ is an electron donating group.

62. The emissive material of claim 56 wherein at least one substituent of the emissive material is an electron donating group selected from alkyl, alkenyl, aryl, heteroaryl, OR, SR, $NR_2$ (including cyclic-amino), and $PR_2$ (including cyclic-phosphino), where R is a hydrogen, alkyl, aryl or heteroaryl group.

63. The emissive material of claim 56 wherein the metal is selected from Ir, Pt, Pd, Rh, Re, Os, Tl, Pb, Bi, In, Sn, Sb, Te, Au, and Ag.

64. The emissive material of claim 56 wherein the metal is iridium.

65. The emissive material of claim 56 wherein the metal is platinum.

66. The composition of claim 56 wherein if neither $R_3$ nor $R_5$ is an electron donating group then $R'_4$ is an electron donating group.

67. The emissive material of claim 66 wherein $R'_4$ is an electron withdrawing group.

68. The emissive material of claim 66 wherein one of $R_3$ and $R_5$ is an electron donating group, and $R'_4$ is an electron withdrawing group.

69. The emissive material of claim 66 wherein at least one substituent of the emissive material is an electron withdrawing group selected from halogens, perfluoroalkyl, trifluorovinyl, $NO_2$, $CO_2R$, $C(O)R$, $S(O)R$, $SO_2R$, $SO_3R$, $P(O)R$, $PO_2R$, $PO_3R$, $C\equiv CR$, and aryl and heteroaryl groups substituted with halogens, CN, perfluoroalkyl, trifluorovinyl, $NO_2$, $CO_2R$, $C(O)R$, $S(O)R$, $SO_2R$, $SO_3R$, $P(O)R$, $PO_2R$, or $PO_3R$, where R is a hydrogen, alkyl, aryl or heteroaryl group.

70. The emissive material of claim 66 wherein at least one substituent of the emissive material is an electron donating group selected from alkyl, alkenyl, aryl, heteroaryl, OR, SR, $NR_2$ (including cyclic-amino), and $PR_2$ (including cyclic-phosphino), where R is a hydrogen, alkyl, aryl or heteroaryl group.

71. The emissive material of claim 66 wherein the metal is selected from Ir, Pt, Pd, Rh, Re, Os, Tl, Pb, Bi, In, Sn, Sb, Te, Au, and Ag.

72. A light emitting device comprising an organic layer, the organic layer comprising a composition represented by the general structure:

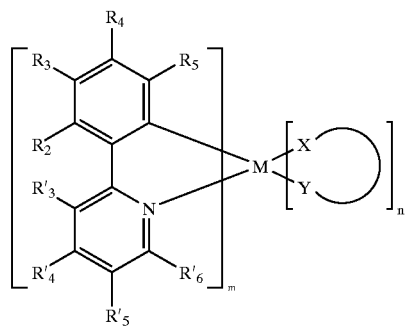

wherein M is a heavy metal with an atomic weight of greater than or equal to 40; m is at least 1 n is at least 0

X-Y is an ancillary ligand;

$R_2$ and $R_4$ are both F;

each of $R_3$, $R_5$, and $R'_3$ through $R'_6$ are independently selected from the group consisting of H, halogens, CN, perfluoroalkyl, trifluorovinyl, $NO_2$, $CO_2R$, $C(O)R$, $S(O)R$, $SO_2R$, $SO_3R$, $P(O)R$, $PO_2R$, $PO_3R$, $C\equiv CR$, alkyl, alkenyl, aryl, heteroaryl, OR, SR, $NR_2$ (including cyclic-amino), and $PR_2$ (including cyclic-phosphino), where R is hydrogen, an alkyl group, an aryl group or a heteroaryl group, wherein at least one of $R_3$ and $R_5$ is CN.

73. The light emitting device of claim 72 wherein if neither $R_3$ nor $R_5$ is an electron donating group then $R'_4$ is an electron donating group.

* * * * *